(12) United States Patent
Utkhede et al.

(10) Patent No.: US 11,406,532 B2
(45) Date of Patent: Aug. 9, 2022

(54) STATIC PIN INSERTION TOOL FOR LACRIMAL IMPLANT

(71) Applicant: Mati Therapeutics Inc., Austin, TX (US)

(72) Inventors: Deepank Utkhede, Burnaby (CA); Jon Wallace, Burnaby (CA); Robert Williams, Friday Harbor, WA (US)

(73) Assignee: Mati Therapeutics Inc., Austin, TX (US)

( * ) Notice: Subject to any disclaimer, the term of this patent is extended or adjusted under 35 U.S.C. 154(b) by 514 days.

(21) Appl. No.: 16/316,563

(22) PCT Filed: Jul. 13, 2017

(86) PCT No.: PCT/US2017/042020
§ 371 (c)(1),
(2) Date: Jan. 9, 2019

(87) PCT Pub. No.: WO2018/013869
PCT Pub. Date: Jan. 18, 2018

(65) Prior Publication Data
US 2019/0247230 A1    Aug. 15, 2019

Related U.S. Application Data

(60) Provisional application No. 62/362,004, filed on Jul. 13, 2016.

(51) Int. Cl.
*A61F 9/007*   (2006.01)
*A61F 9/00*    (2006.01)
*A61F 2/00*    (2006.01)

(52) U.S. Cl.
CPC ........ *A61F 9/00772* (2013.01); *A61F 9/0017* (2013.01); *A61F 2/0095* (2013.01); *A61F 2250/0067* (2013.01)

(58) Field of Classification Search
CPC .. A61F 9/00772; A61F 9/0017; A61F 2/0095; A61F 2250/0067; A61F 2250/0065; A61F 2250/0058; A61F 2/46; A61F 2002/4638; A61F 2002/4641;
(Continued)

(56) References Cited

U.S. PATENT DOCUMENTS

| | | | | |
|---|---|---|---|---|
| 4,096,896 A | * | 6/1978 | Engel | B25B 15/00 81/121.1 |
| 5,971,987 A | * | 10/1999 | Huxel | A61B 17/8605 411/2 |
| 10,406,028 B1 | * | 9/2019 | Becker | A61F 9/00772 |

(Continued)

*Primary Examiner* — Adam Marcetich
(74) *Attorney, Agent, or Firm* — Koren Anderson

(57) ABSTRACT

An insertion tool, systems, and methods for use with lacrimal implants are herein provided. An insertion tool is disclosed that includes an inserter tip with a static pin at a distal end configured to be placed in a bore of a lacrimal implant and a mechanical coupling to receive a handle at a proximal end of the inserter tip; and, a handle coupled to the inserter tip at a distal end of the handle and a plunger at a proximal end of the handle, wherein the plunger is configured to release the inserter tip from the handle. The static pin of the inserter tip is de-coupled from the lacrimal implant after placement in a lacrimal canaliculus without mechanical force from the insertion tool.

36 Claims, 21 Drawing Sheets

(58) Field of Classification Search
CPC ............. A61M 27/002; B25B 23/0035; B25B 23/0057; B25F 1/02
See application file for complete search history.

(56) References Cited

U.S. PATENT DOCUMENTS

| | | | |
|---|---|---|---|
| 2007/0106283 A1* | 5/2007 | Garcia | A61B 17/8883 606/1 |
| 2008/0045970 A1* | 2/2008 | Saidha | A61B 17/7082 606/104 |
| 2009/0112217 A1* | 4/2009 | Hester | A61F 2/4611 606/99 |
| 2010/0209477 A1* | 8/2010 | Butuner | A61K 31/216 424/427 |
| 2011/0112546 A1* | 5/2011 | Juan, Jr. | A61F 9/0017 606/108 |
| 2011/0137305 A1* | 6/2011 | Hernandez Zendejas | A61B 18/148 606/30 |
| 2013/0023837 A1* | 1/2013 | Becker | A61F 9/00772 604/294 |
| 2013/0053794 A1* | 2/2013 | Cadden | A61K 9/0092 604/290 |
| 2015/0216722 A1* | 8/2015 | Choate | A61F 9/00772 606/162 |
| 2017/0273825 A1* | 9/2017 | Yamamoto | A61F 9/0008 |

* cited by examiner

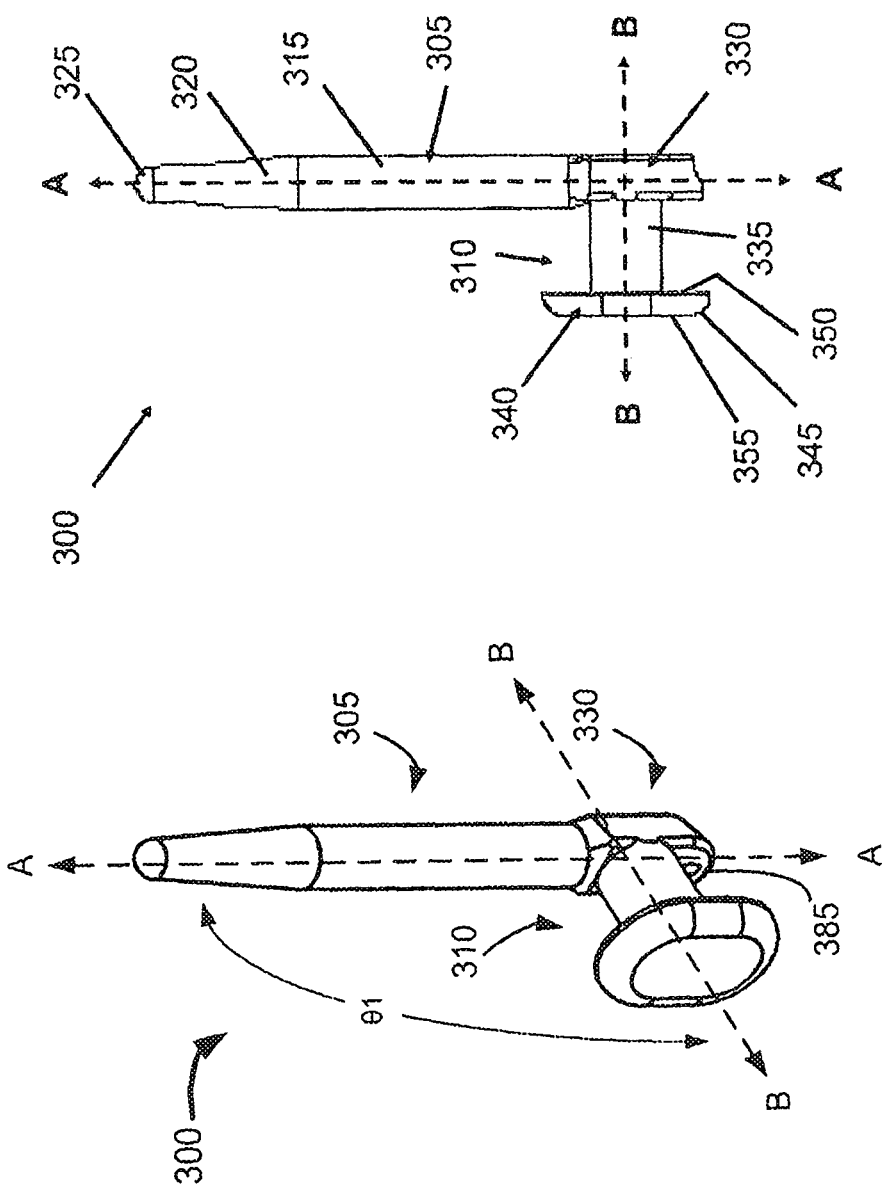

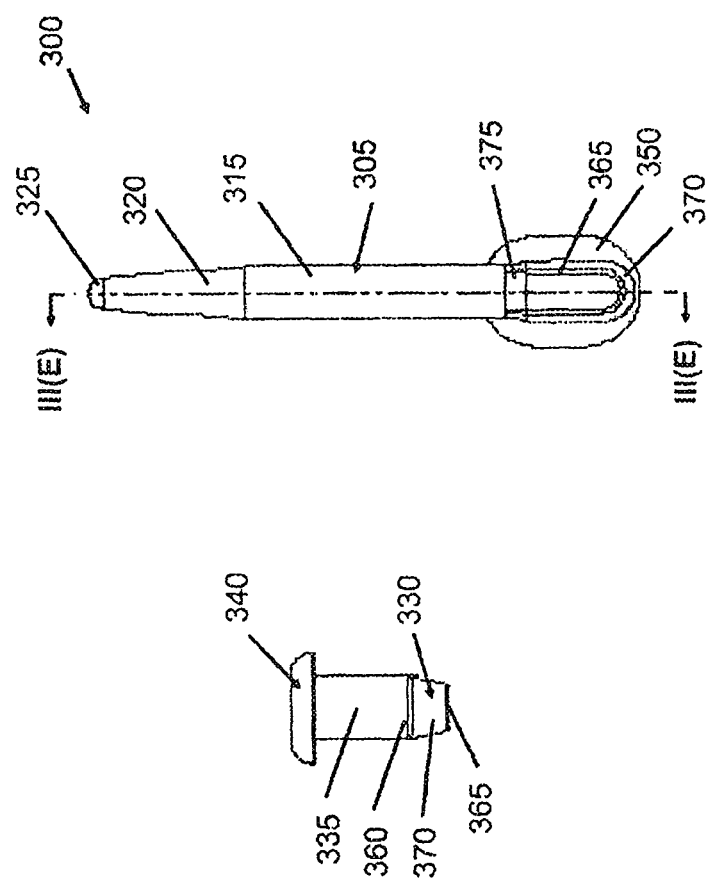

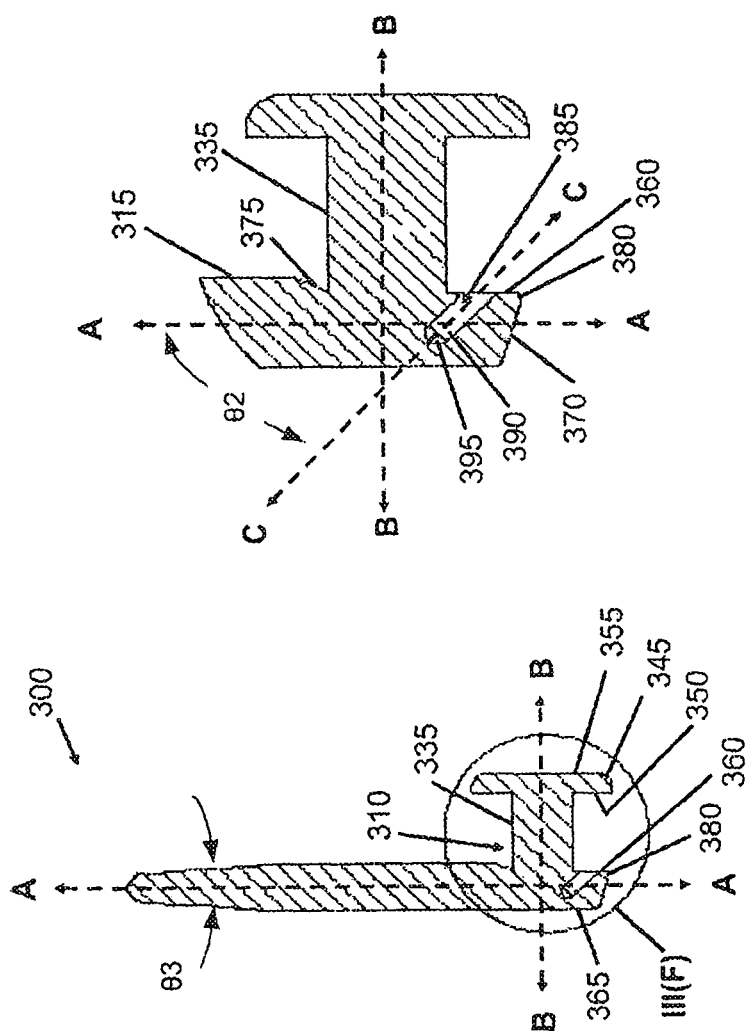

STATIC PIN INSERTION TOOL FOR LACRIMAL IMPLANT

CROSS-REFERENCE TO RELATED APPLICATIONS

This application claims the benefit of U.S. Provisional Patent Application No. 62/362,004, filed on 13 Jul. 2016, the contents of which is incorporated herein by reference in its entirety.

FIELD OF THE INVENTION

This application pertains generally to insertion tools for placement of lacrimal implants and/or punctal plugs and their uses thereof for methods of treating ocular diseases and conditions.

BACKGROUND OF THE INVENTION

Lacrimal implants are devices that are inserted into a punctum and an associated lacrimal canaliculus of an eye, either to block drainage of tears (to prevent conditions such as dry eye), or to contain a quantity of drug for topical release into the eye, administration into the surrounding tissue of the eye or systemically via drainage of the lacrimal canaliculus.

FIGS. 1-2 illustrate example views of anatomical tissue structures associated with an eye 100. Certain of the anatomical tissue structures shown may be suitable for treatment using the various lacrimal implants and methods discussed herein. The eye 100 is a spherical structure including a wall having three layers: an outer sclera 102, a middle choroid layer 104 and an inner retina 106. The sclera 102 includes a tough fibrous coating that protects the inner layers. It is mostly white except for the transparent area at the front, commonly known as the cornea 108, which allows light to enter the eye 100.

The choroid layer 104, situated inside the sclera 102, contains many blood vessels and is modified at the front of the eye 100 as a pigmented iris 110. A biconvex lens 112 is situated just behind the pupil. A chamber 114 behind the lens 112 is filled with vitreous humor, a gelatinous substance. Anterior and posterior chambers 116 are situated between the cornea 108 and iris 110, respectively and filled with aqueous humor. At the back of the eye 100 is the light-detecting retina 106.

The cornea 108 is an optically transparent tissue that conveys images to the back of the eye 100. It includes a vascular tissue to which nutrients and oxygen are supplied via bathing with lacrimal fluid and aqueous humor as well as from blood vessels that line the junction between the cornea 108 and sclera 102. The cornea 108 includes a pathway for the permeation of drugs into the eye 100.

Turning to FIG. 2, other anatomical tissue structures associated with the eye 100 including the lacrimal drainage system, which includes a secretory system 230, a distributive system and an excretory system, are shown. The secretory system 230 comprises secretors that are stimulated by blinking and temperature change due to tear evaporation and reflex secretors that have an efferent parasympathetic nerve supply and secrete tears in response to physical or emotional stimulation. The distributive system includes the eyelids 202 and the tear meniscus around the lid edges of an open eye, which spread tears over the ocular surface by blinking, thus reducing dry areas from developing.

The excretory system of the lacrimal drainage system includes, in order of flow, drainage, the lacrimal puncta, the lacrimal canaliculi, the lacrimal sac 204 and the lacrimal duct 206. From the lacrimal duct 206, tears and other flowable materials drain into a passage of the nasolacrimal system. The lacrimal canaliculi include an upper (superior) lacrimal canaliculus 208 and a lower (inferior) lacrimal canaliculus 210, which respectively terminate in an upper 212 and lower 214 lacrimal puncta. The upper 212 and lower 214 puncta are slightly elevated at the medial end of a lid margin at the junction 216 of the ciliary and lacrimal portions near a conjunctival sac 218. The upper 212 and lower 214 puncta are generally round or slightly ovoid openings surrounded by a connective ring of tissue. Each of puncta 212 and 214 leads into a vertical portion 220, 222 of their respective canaliculus before turning more horizontal at a canaliculus curvature 250 to join one another at the entrance of the lacrimal sac 204. The canaliculi 208, 210 are generally tubular in shape and lined by stratified squamous epithelium surrounded by elastic tissue, which permits them to be dilated. As shown, a lacrimal canaliculus ampulla 252 exists near an outer edge of each canaliculus curvature 250.

A variety of challenges face patients and physicians in the area of ocular drug delivery. In particular, the repetitive nature of the therapies (multiple injections, instilling multiple eye drop regimens per day), the associated costs, and the lack of patient compliance may significantly impact the efficacy of the therapies available, leading to reduction in vision and many times blindness.

Patient compliance in taking the medications, for example instilling the eye drops, can be erratic, and in some cases, patients may not follow the directed treatment regime. Lack of compliance can include, failure to instill the drops, ineffective technique (instilling less than required), excessive use of the drops (leading to systemic side effects), and use of non-prescribed drops or failure to follow the treatment regime requiring multiple types of drops. Many of the medications may require the patient to instill them up to 4 times a day.

One promising approach to ocular drug delivery is use of non-invasive (e.g. non-surgical) implants placed in tissue on or near the eye that topically releases a drug the eye. These implants can be placed in the lacrimal canaliculus (vertical and/or horizontal portions thereof) or on the ocular surface of the eye (e.g. conjunctiva tissue under the eye lid or over the cornea). Although this approach can offer some improvement over eye drops, some potential problems of this approach using punctal plug implants may include placement of the implant at the desired tissue location, retention of the implant at the desired tissue location, and sustaining release of the drug at the desired therapeutic level for an extended period of time.

One problem in particular with punctal plug lacrimal implants, especially those that elute drug from a surface in contact with tear fluid, such as an exposed proximal end, is the difficulty inserting them into the punctum. Punctal plugs are configured to fit at least partially within the lacrimal canaliculus and due to their small size are difficult to handle without the aid of a tool. They may also be difficult to orient that cannot be managed with forceps or tweezers. The size and shape of the lacrimal canaliculus is not uniform, and to increase retention of the implant, some implants have been designed based on the unique shape of the lacrimal canaliculus and must be placed in a certain orientation or configuration. Placement of those punctal plugs requires an insertion tool that is easy to handle by the end user and facilitates correct placement and orientation of the punctal plug.

In light of the above, it would be desirable to provide an improved insertion and/or extraction tool for lacrimal implants that overcome at least some of the above mentioned shortcomings.

SUMMARY OF THE INVENTION

In an exemplary embodiment, the present invention provides insertion tools, a system for treating eye disease and a method for placement of a lacrimal implant using the insertion tools. In embodiments, the insertion tool comprises an inserter tip comprising a static pin at a distal end configured for placement in a bore of a lacrimal implant and a mechanical coupling to receive a handle at a proximal end of the inserter tip; and, a handle coupled to the inserter tip at a distal end of the handle and a plunger at a proximal end of the handle, wherein the plunger is configured to release the inserter tip from the handle. In embodiments, the handle comprises a spring and a screw in a lumen of the handle and the proximal end of the inserter tip is configured to be placed and secured via an interference or friction fit within the lumen of the distal end of the handle wherein the head of the screw provide resistance to plunger. The plunger is configured to slide within the lumen of the handle, engage the spring and release the inserter tip from the handle.

In embodiments, the insertion tool further comprises a lacrimal implant coupled to the static pin of the inserter tip. In embodiments, the lacrimal implant comprises a first member defining a first axis and having a first end along the first axis, wherein the first member is configured to extend into the canaliculus; a second member defining a second axis and having a second end along the second axis, wherein the second member is configured to reside in a vertical portion of the canaliculus and to extend to an opening of, or out of the opening of, an associate lacrimal punctum; a cavity that is configured to house a therapeutic agent core, wherein the cavity extends into the second member along the second axis; a third member connecting the first end of the first member and the second end of the second member at a first angle to form an angled intersection; the third member comprises a bore defining a third axis and a second angle and having an upper surface; wherein the bore is configured to be accessible to the static pin of the inserter tip for facilitating insertion of the implant and extends from the upper surface into the third member; and further wherein the first angle is defined by the first axis with respect to the second axis and the second angle is defined by the first axis with respect to the third axis; wherein the first angle is from 30 degrees to 150 degrees; and wherein the second angle is from 15 degrees to 90 degrees.

In embodiments, the inserter tip is coupled to a lacrimal implant providing a system for treatment of an eye disease or disorder. In embodiments, the system further comprises sterile packaging. In embodiments, the system comprises an inserter tip comprising a static pin at a distal end configured to be placed in a bore of a lacrimal implant and a mechanical coupling to receive a handle at a proximal end of the inserter tip; and a lacrimal implant coupled to the static pin of the inserter tip. In embodiments, the system further comprises a handle coupled to the inserter tip at a distal end of the handle and a plunger at a proximal end of the handle, wherein the plunger is configured to release the inserter tip from the handle. The handle comprises a spring and a screw in a lumen of the handle, and the proximal end of the inserter tip is configured to be placed around the head of the screw to provide resistance to the plunger and handle. In embodiments, the plunger is configured to slide within the lumen of the handle, engage the spring and release the inserter tip from the handle.

In embodiments, the insertion tool is used to place a lacrimal implant in a punctum and lacrimal canaliculus of a subject comprising, coupling the system comprising a lacrimal implant and an inserter tip, to a handle, wherein the handle is coupled to the inserter tip at a distal end of the handle and the handle comprises a plunger at a proximal end of the handle, wherein the plunger is configured to release or discard the inserter tip from the handle (after removal or de-coupling of the insertion tool and lacrimal implant); placing the lacrimal implant in a punctum; and de-coupling the inserter tip from the lacrimal implant wherein the static pin is released without mechanical force from the insertion tool. In embodiments, the pin coupled to the lacrimal implant is static where a force is exerted by the user to release the pin from the friction fit of the pin in the bore of the lacrimal implant by gently pulling back on the handle away from the lacrimal implant. In embodiments, the lacrimal implant is punctal plug of those represented in FIGS. 3 to 6. Those lacrimal implants are well retained in the punctum due to their unique design and gently pulling back on the handle of the insertion tool does not dislodge the punctal plug from the punctum. The instant insertion tool is designed to be used with those plugs that comprise at least an L-shape (e.g., a first and second member) that sit in both the vertical and horizontal section of the lacrimal canaliculus, and a heal (e.g. a third member) that fits into the ampulla of the lacrimal canaliculus. See FIG. 2. The design of those plugs provides a retention rate in the punctum of at least 80%, at least 85%, at least 90% or at least 95% over a period of 4 weeks. See U.S. Pat. No. 9,610,271 at FIG. 12, herein incorporated by reference.

In various embodiments, the invention includes a kit having an implant of the invention and an insertion tool for inserting the implant into the punctum.

Also provided is a method of treating an ocular disease using one or more punctal implant.

These and other embodiments, advantages, and aspects of the methods disclosed herein are set forth in part in following detailed description.

BRIEF DESCRIPTION OF THE DRAWINGS

In the drawings, like numerals describe similar components throughout the several views. Like numerals having different letter suffixes represent different instances of similar components. The drawings illustrate generally, by way of example, but not by way of limitation, various embodiments disclosed herein.

FIG. 3A provides a perspective view of an implant in accordance with an embodiment of the present invention.

FIG. 3B is a side view of an implant in accordance with an embodiment of the present invention.

FIG. 3C is a side view illustrating the second member and the third member of an implant in accordance with an embodiment of the present invention.

FIG. 3D is a back view of an implant in accordance with an embodiment of the present invention.

FIG. 3E is a cross-sectional view taken about line III(E)-III(E) of FIG. 3D depicting an implant with a bore, in accordance with an embodiment of the present invention.

FIG. 3F is a partially enlarged view of FIG. 3E taken about circle III(F) depicting the second member, the third member and a bore formed in the third member of an implant, in accordance with an embodiment of the present invention.

DETAILED DESCRIPTION OF THE INVENTION

Figure 9:
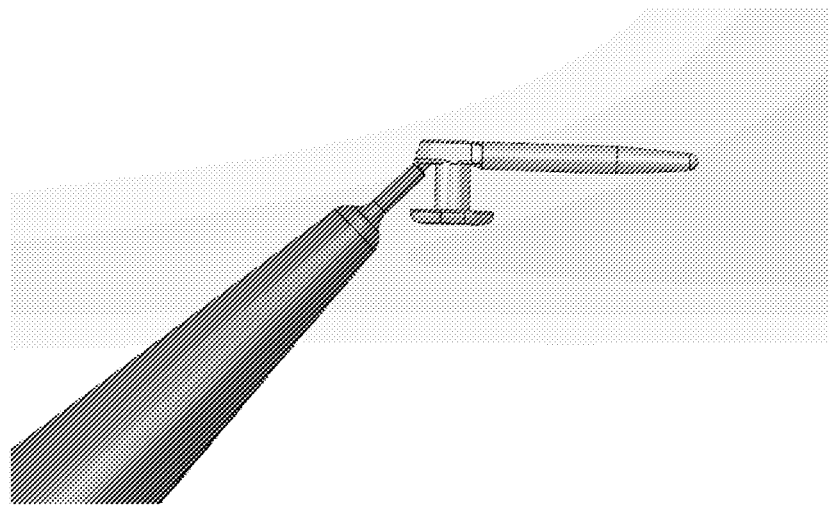
FIG. 9 provides a view of the inserter tip and static pin coupled to a lacrimal implant.
Figure 12:
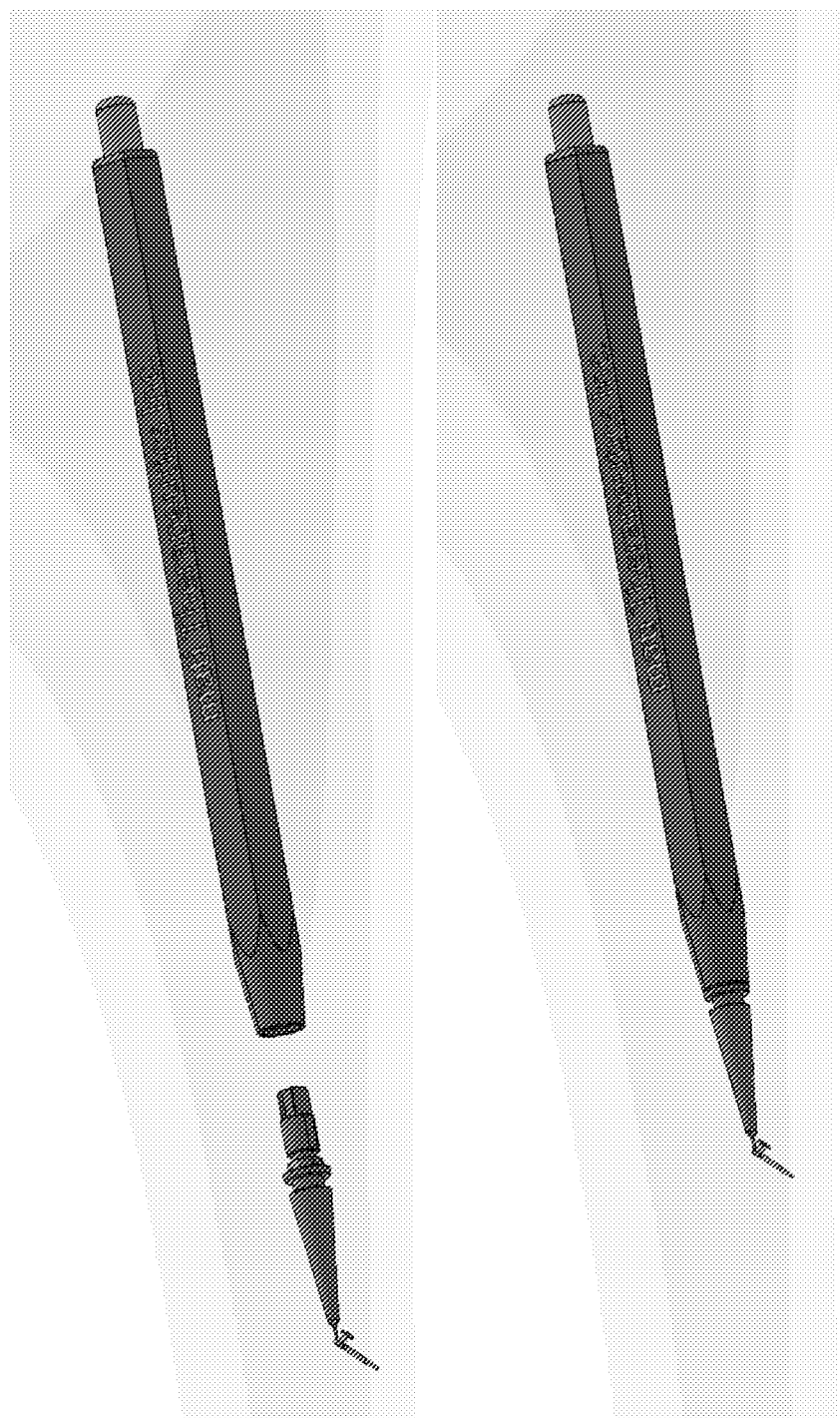
FIG. 12 provides a view of a lacrimal implant coupled to the static pin of the inserter tip, a handle and coupling of the inserter tip and handle.
Figure 14:
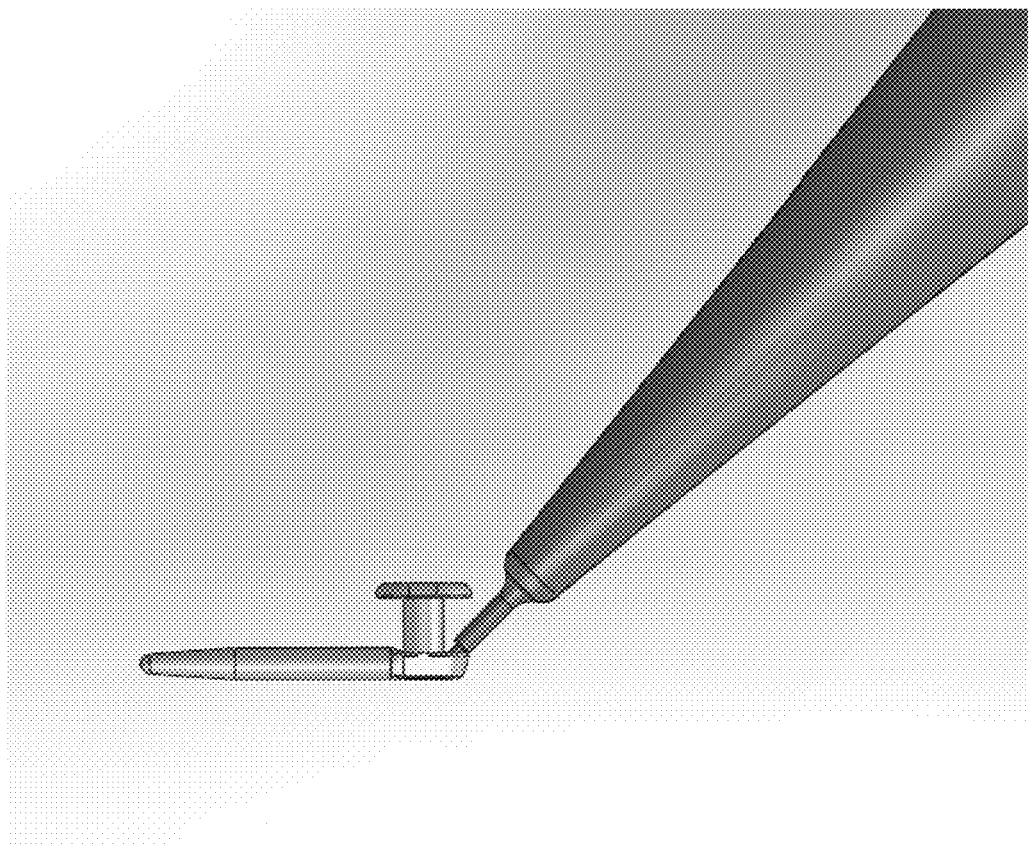
FIG. 14 provides a view of the inserter tip and static pin coupled to a lacrimal implant.

In an exemplary embodiment of the present invention, there is provided compositions, kits and methods of using the compositions. Provided herein are insertion tools for the placement of punctal plug lacrimal implants into a puncta and lacrimal canaliculus of a subject. The lacrimal implants, described in more detail below, were developed to overcome a number of limitations of commercially available punctal plugs such as retention rate and a cavity and/or reservoir large enough to hold a drug core. The improved retention rate for the lacrimal implants of the present invention is due to a number of prominent features on the punctal plugs which include a long leg (305) that guides the plug into the canaliculus, a large heel (380) for placement in the ampulla of the lacrimal canaliculus which keeps the plug from slipping out of the punctum and a large hat (occlusive element; 340) which prevents the plug from slipping into punctal duct. See FIGS. 3-6. Although these features improve the retention of the lacrimal implant, they also make the punctal plug more difficult to place in the puncta necessitating the use of an insertion tool to aid the clinician during the placement. This is further complicated by the fact that most commercial punctal plug inserters are designed to use the bore (e.g., 458) that houses the present drug core. Thus, an alternative placement for the attachment of the punctal plug to the insertion tool was incorporated into the present plug design. See FIGS. 6 and 385 defining the bore for the static pin of the present insertion tool. The instant lacrimal implant comprises a bore in the heel of the plug which is designed to accommodate the pin of the inserter. See FIGS. 9, 12 and 14.

Figure 8:
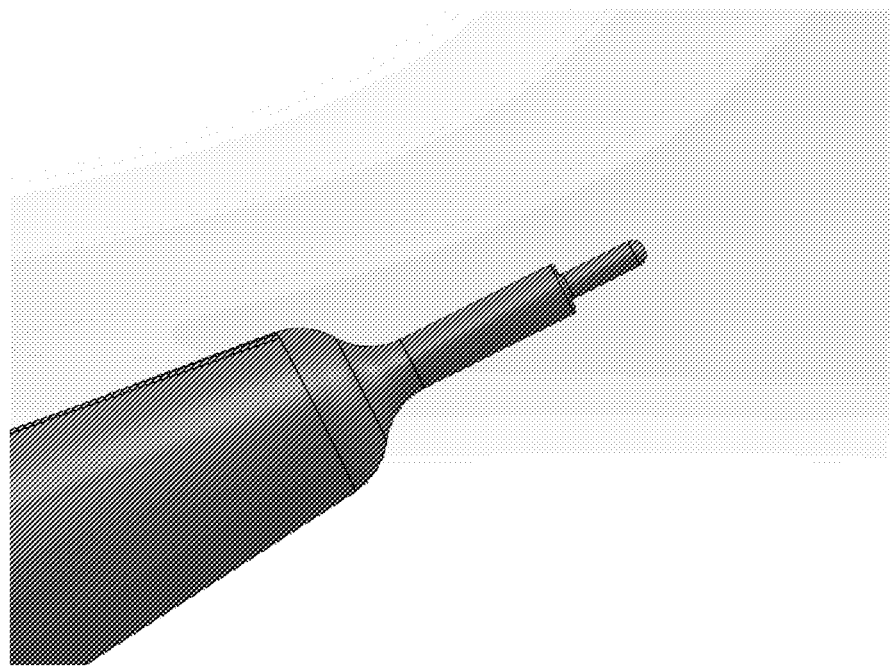
FIG. 8 provides a view of the static pin of the inserter tip.
Figure 13:
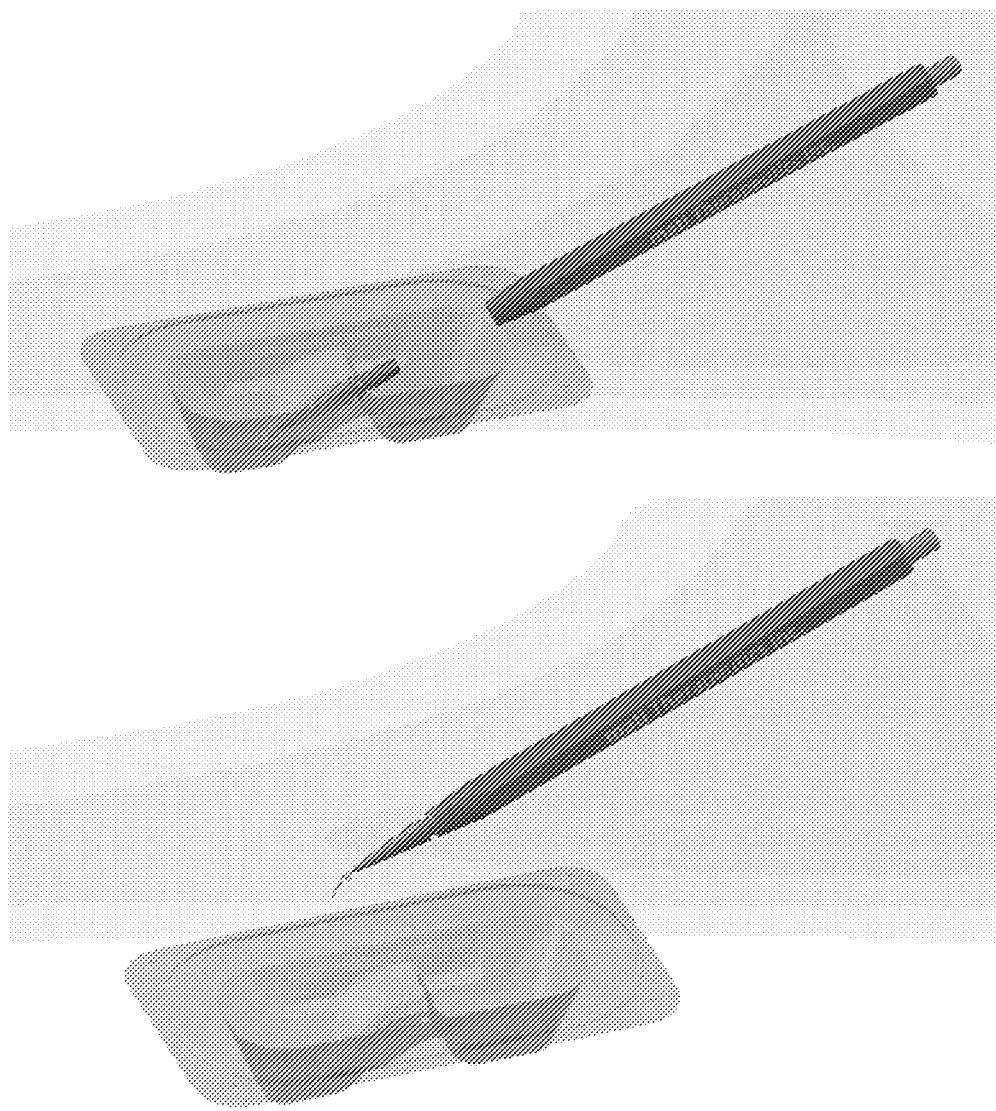
FIG. 13 provides a view of a system (inserter tip coupled to a lacrimal implant) in packaging, a handle and coupling of the inserter tip and handle while the inserter tip is in the packaging.

The present static punctal plug inserter comprises a static pin at the distal end of the inserter tip and is configured to improve the user's ability to hold and manipulate the punctal plug during insertion into a subject's puncta. In embodiments, the inserter is a two-piece design with a disposable tip and handle. See FIGS. 12 and 13. In certain embodiments the handle is reusable and in other embodiments the handle is disposable. In certain embodiments, the inserter tip comprises a static pin at the distal end and at the proximal end a piece that fits into the distal end of the handle of the insertion tool. See FIG. 8. The static pin is configured for placement and fit into a bore of the lacrimal implant. See 385 of FIG. 6.

Figure 15:
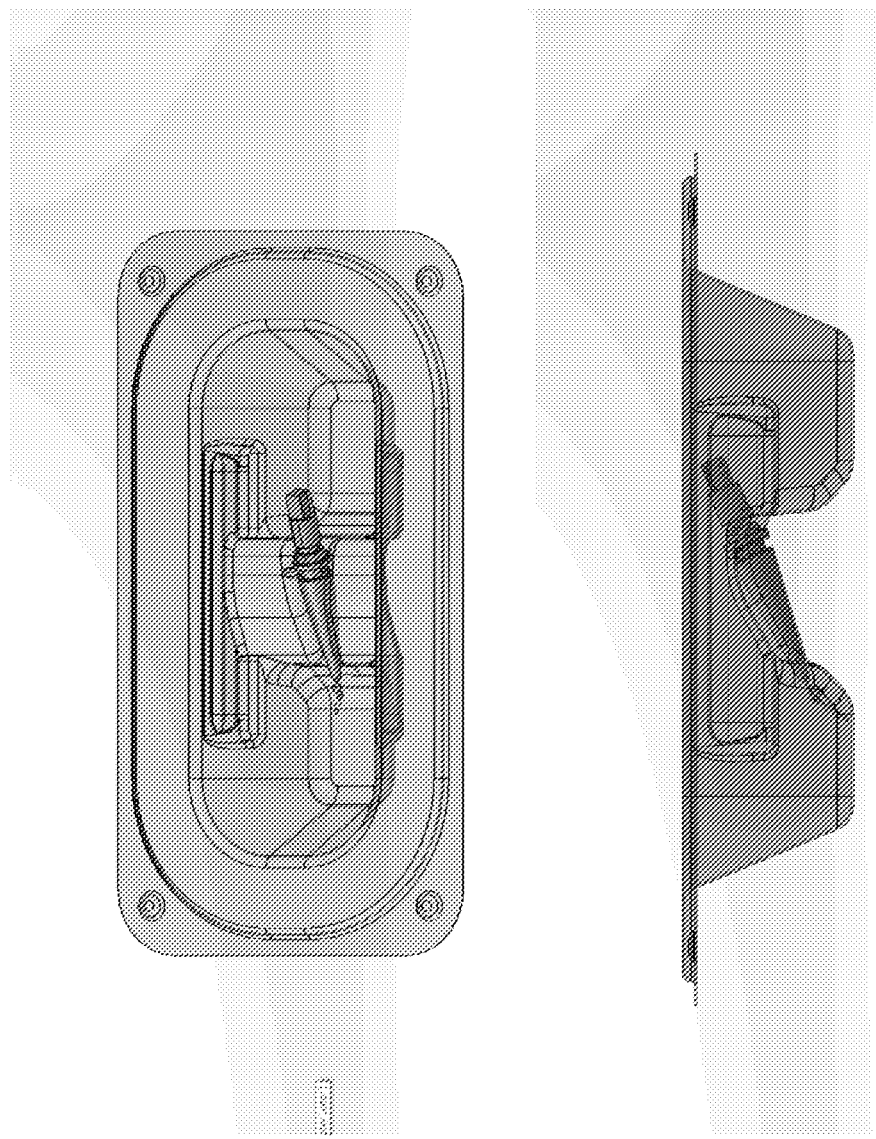
FIG. 15 provides a view of the inserter tip ad static pin coupled to a lacrimal implant placed in packaging.

In embodiments, the lacrimal implant can be coupled to the static pin of the inserter tip and be packaged into a rigid tray and heat sealed with an aluminum laminate or a Tyvek lid. See FIG. 15. The product is then terminally sterilized, such as with e-beam or gamma irradiation, ethylene oxide or steam. In embodiments, the handle is provided in a separate package.

Figure 16:
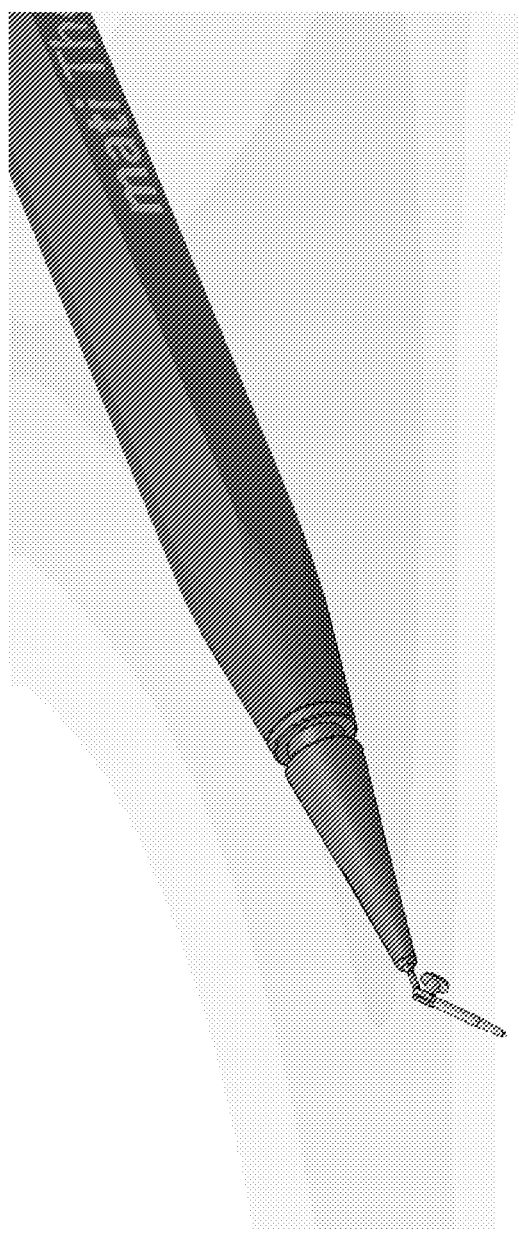
FIG. 16 provides a view of the inserter tip and static pin coupled to a lacrimal implant.
Figure 17:
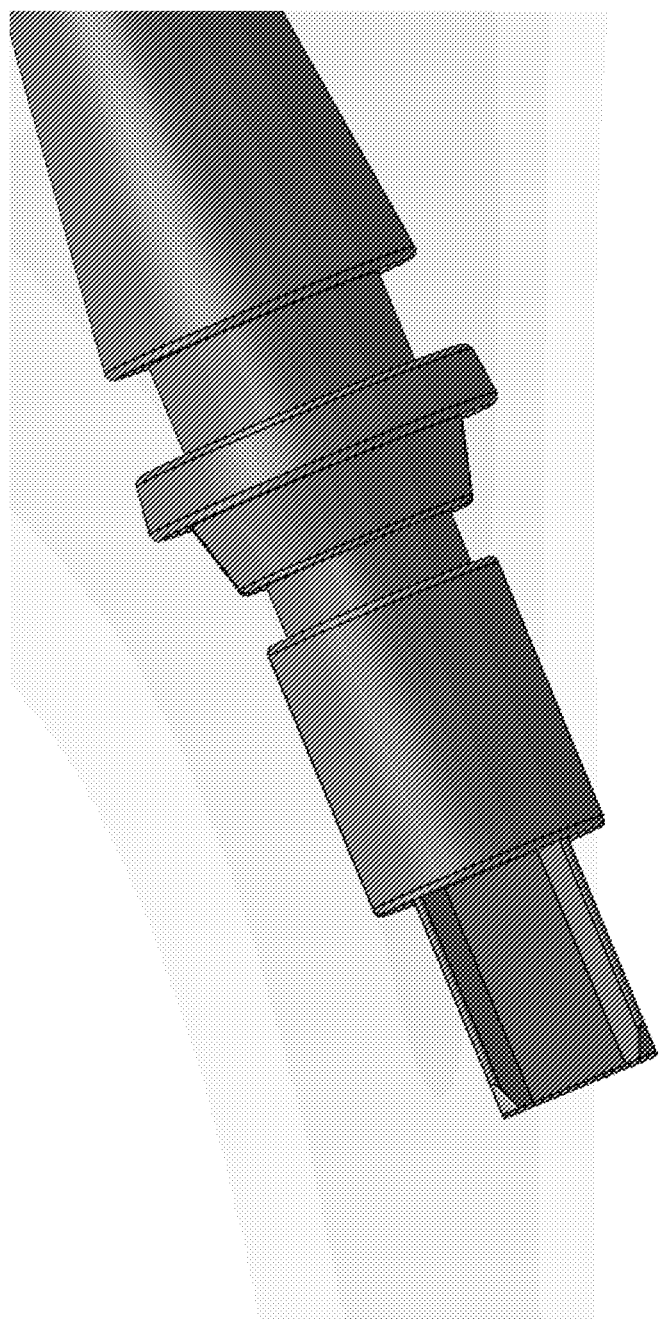
FIG. 17 provides a magnified view of the proximal end of the inserter tip.
Figure 18:
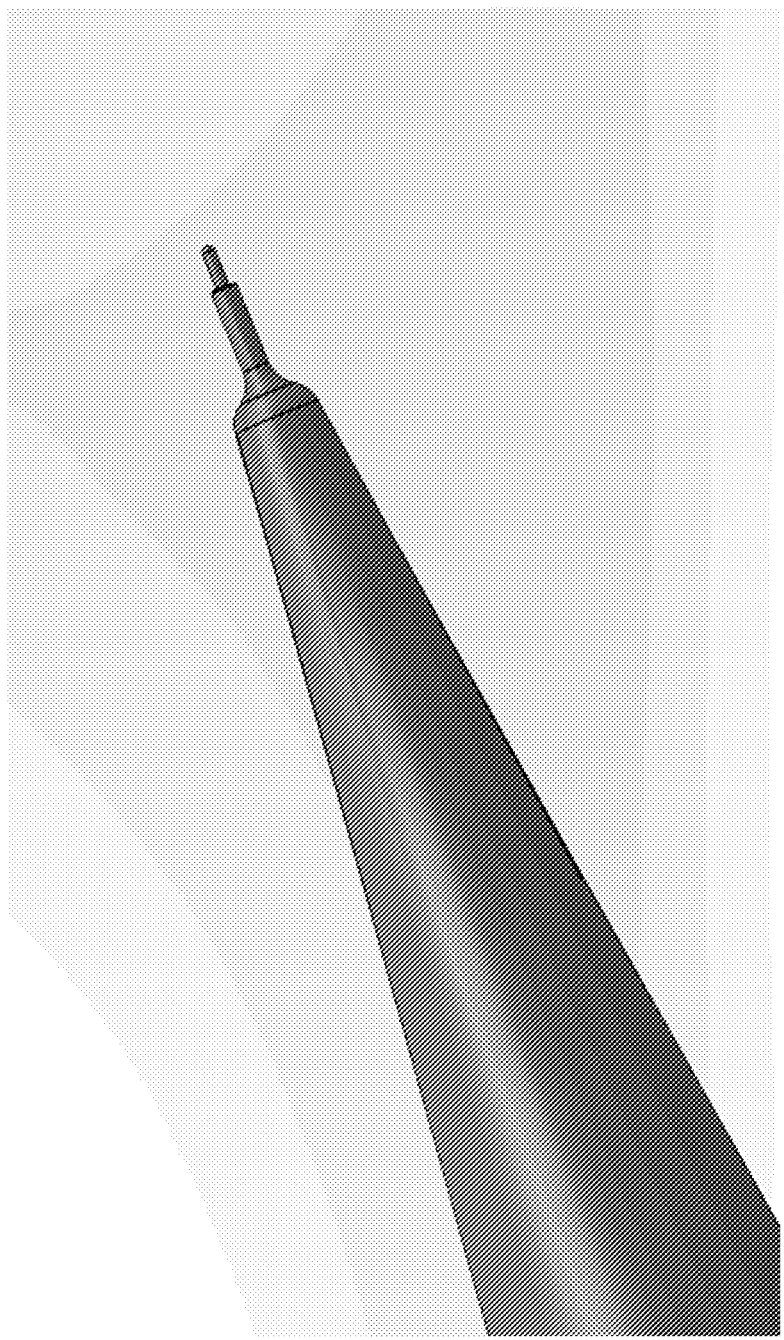
FIG. 18 provides a magnified view of the distal end of the inserter tip and static pin.

In embodiments, methods of use include opening the packaging containing the punctal plug coupled to the inserter tip followed by attachment of the handle to the inserter tip. See FIGS. 12, 13 and 16. In embodiments, the inserter tip can be attached to the handle without the need to first remove the punctal plug from its packaging. Once the inserter tip and handle are coupled a user can then place the implant in a punctum of a subject. In alternative embodiments, the static inserter is provided as one piece and the punctal plug is provided separately in sterile packaging. In that instance, the static inserter may either be reusable or disposable. In other embodiments are provided packaging comprising the lacrimal implant coupled to the inserter tip that is coupled to the handle.

Figure 11:
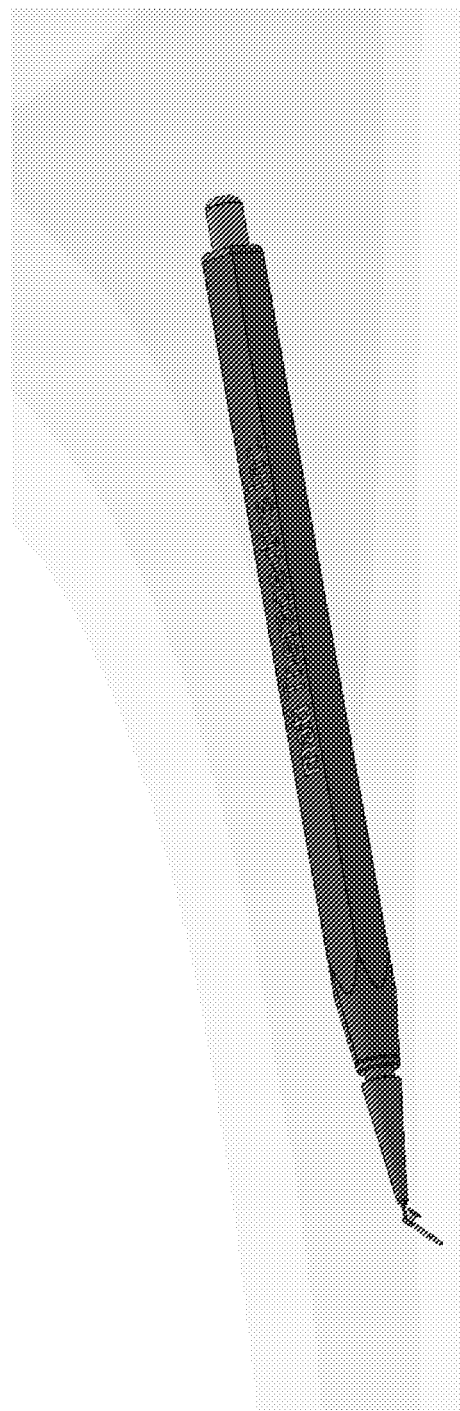
FIG. 11 provides a view of the insertion tool wherein the inserter tip is coupled to the handle.

In embodiments, is provided an insertion tool comprising an inserter tip comprising a static pin at a distal end configured to be placed in a bore of a lacrimal implant and a mechanical coupling to receive a handle at a proximal end of the inserter tip; and, a handle coupled to the inserter tip at a distal end of the handle and a plunger at a proximal end of the handle, wherein the plunger is configured to release the inserter tip from the handle. See FIGS. 7 and 11. In embodiments, the handle comprises a spring and a screw in a lumen of the handle. See FIG. 7. In embodiments, the plunger is configured to slide within the lumen of the handle, engage the spring and release the inserter tip from the handle. In embodiments, the inserter tip and handle and coupled via an interference or friction fit.

Figure 10:
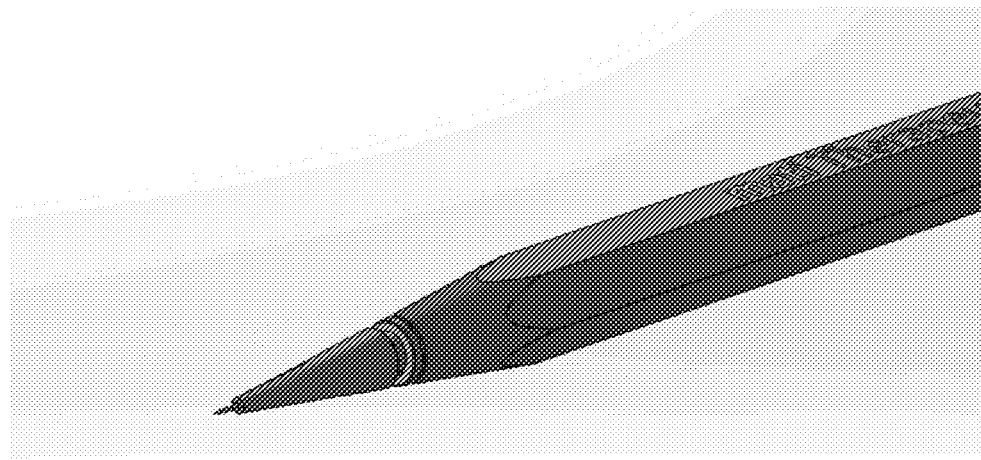
FIG. 10 provides a view of the inserter tip coupled to the handle of the insertion tool.

In embodiments, the inserter tip has a cone shaped first part with a small static pin at a distal end. See FIG. 10. In embodiments, the inserter tip is a unitary body with no movable parts. The lacrimal implant can be coupled to the pin and is secured with a friction fit. The cone feature can act as a transition in diameter from the pin to the handle. In embodiments, the proximal end of the inserter tip comprises a retention feature for removable attachment of the inserter tip to the distal end of the handle. In embodiments, the retention feature is configured to fit over and couple to a screw or pin within a lumen of the handle. In alternative embodiments, the inserter tip is coupled to the handle via an interference fit, wherein the screw/spring/plunger configuration is used to remove the tip from the handle.

In embodiments, the inserter tip is disposable and once the lacrimal implant is placed in a subject's puncta the tip can be ejected or removed from the handle. In embodiments, the insertion tool comprises a spring-loaded button or plunger for ejecting the inserter tip from the handle. See FIG. 7. In alternative embodiments, the inserter tip may be permanently or temporarily attached to the handle wherein the tip is reusable and not disposed of after one use. In embodiments, there are no moving or movable parts of the inserter tip once the insertion tool is fully assembled. In embodiments, the pin of the inserter tip is static and is not a movable piece of the insertion tool. Due to the design of the present lacrimal implants, once the punctal plug is placed in the puncta of the subject, the user can remove the static inserter without mechanical force, while the implant remains securely placed in a lacrimal canaliculus of a subject. The unique design of the punctal plugs remain securely placed in the punctal via an interference fit allowing a user to pull back on the insertion tool to separate it from the punctal plug.

Figure 7:
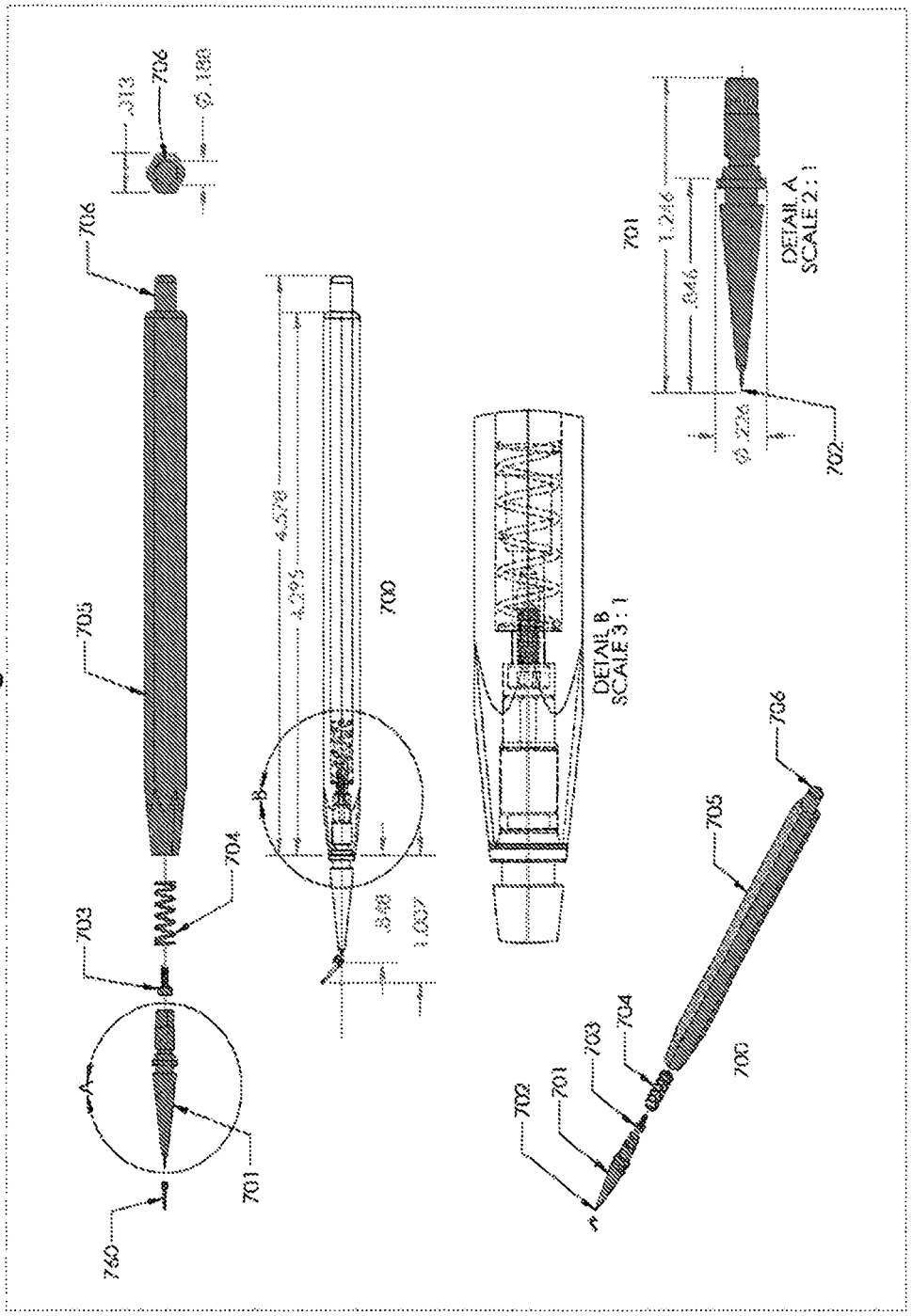
FIG. 7 provides an example of a static insertion tool and engagement with an implant in accordance with an embodiment of the present invention.

FIG. 7 shows embodiments of the static insertion tool that can be used to place lacrimal implants through a punctum and into a lacrimal canaliculus of a subject. In embodiments, the insertion tool comprises a removable inserter tip with a static pin, wherein the pin is configured to fit into a bore of the lacrimal implant. In embodiments, the insertion tool comprises a spring-loaded button or mechanism for removal of the inserter tip from the handle.

Also disclosed herein are exemplary structures of lacrimal implants of use in the methods of the invention for treating various ocular diseases and disorders. Exemplary structures include lacrimal implants for at least partial insertion through the lacrimal punctum and into its associated canaliculus. Various embodiments further provide an insertion tool for placing a lacrimal implant into a lacrimal punctum. Also disclosed herein are exemplary implants including therapeutic agents incorporated throughout the device, within one or more section of the device, or in a therapeutic agent core, e.g., a localized therapeutic agent core. The devices of the invention are of use for treating various diseases.

In the various embodiments of methods of the invention, placing a lacrimal implant of the invention through the lacrimal punctum and into its associated canaliculus, in various embodiments, inhibits or blocks tear flow therethrough. In various embodiments, a device inhibiting or blocking tear flow is of use to treat dry eye. In an exemplary embodiment, the insertion of the lacrimal implant allows for the delivery of a therapeutic agent. In various embodiments, the delivery is sustained delivery. Exemplary therapeutic agents incorporated into the implants of the invention are of use to treat the eye, or they can be of use more broadly as systemic therapies. For example, using a device of the invention, the therapeutic agent can be delivered to a nasal passage, to an inner ear system, or to other passages or systems for treatment of various diseases including, but not limited to, eye infection, eye inflammation, glaucoma, other ocular diseases, other ocular disorders, a sinus or allergy disorder, dizziness or a migraine. The devices of the invention are of use for systemic delivery of one or more therapeutic agents in an amount having therapeutic efficacy. In embodiments, the lacrimal implants of the invention are of use for topical delivery of one or more therapeutic agents in an amount having therapeutic efficacy to an eye.

Those of ordinary skill in the art will understand that the following detailed description of the present invention is illustrative only and is not intended to be in any way limiting. Other embodiments of the present invention will readily suggest themselves to such skilled persons having benefit of this disclosure. Reference will now be made in detail to implementations of the present invention as illustrated in the accompanying drawings. The same reference indicators will be used throughout the drawings and the following detailed description to refer to the same or like parts.

Definitions

As used herein, the terms "a" or "an" are used, as is common in patent documents, to include one or more than one, independent of any other instances or usages of "at least one" or "one or more."

As used herein, the term "or" is used to refer to a nonexclusive or, such that "A or B" includes "A but not B," "B but not A," and "A and B," unless otherwise indicated.

As used herein, the term "about" is used to refer to an amount that is approximately, nearly, almost, or in the vicinity of being equal to or is equal to a stated amount, e.g., the state amount plus/minus about 5%, about 4%, about 3%, about 2% or about 1%.

As used herein, an "axis" refers to a general direction along which a member extends. According to this definition, the member is not required to be entirely or partially symmetric with respect to the axis or to be straight along the direction of the axis. Thus, in the context of this definition, any member disclosed in the present application characterized by an axis is not limited to a symmetric or a straight structure.

In this document, the term "proximal" when used in conjunction with the punctal plug or lacrimal implant refers to a location relatively closer to the cornea of an eye, and the term "distal" refers to a location relatively further from the cornea and inserted deeper into a lacrimal canaliculus. In contrast, the term "proximal" wherein used in conjunction with the insertion tool, refers to a location relatively closer to the user, e.g. end of handle farthest from inserter tip, and the term "distal" refers to a location relatively further from the user, e.g. inserter tip.

In the appended claims, the terms "including" and "in which" are used as the plain-English equivalents of the respective terms "comprising" and "wherein." Also, in the following claims, the terms "including" and "comprising" are open-ended, that is, a system, assembly, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

As used herein, the phrase "consisting essentially of" limits a composition to the specified materials or steps and those additional, undefined components that do not materially affect the basic and novel characteristic(s) of the composition.

As used herein, the term "continuous" or "continuously" means essentially unbroken or uninterrupted. For example, continuously administered active agents are administered over a period of time essentially without interruption.

As used herein, the term "diameter" encompasses a broad meaning. For example, with respect to a member having a circular cross section, the term "diameter" has the conventional meaning and refers to a straight line through the center of the circle connecting two points on the circumference. When the cross section is not a circle, the term "diameter" in the present disclosure refers to the characteristic diameter of the cross section. The "characteristic diameter" refers to the diameter of a circle that has the same surface area as the cross section of the element. In the present application, "diameter" is interchangeable with "characteristic diameter."

As used herein, the term "eye" refers to any and all anatomical tissues and structures associated with an eye. The eye is a spherical structure with a wall having three layers: the outer sclera, the middle choroid layer and the inner retina. The sclera includes a tough fibrous coating that protects the inner layers. It is mostly white except for the transparent area at the front, the cornea, which allows light to enter the eye. The choroid layer, situated inside the sclera, contains many blood vessels and is modified at the front of the eye as the pigmented iris. The biconvex lens is situated just behind the pupil. The chamber behind the lens is filled with vitreous humour, a gelatinous substance. The anterior and posterior chambers are situated between the cornea and iris, respectively and filled with aqueous humour. At the back of the eye is the light-detecting retina. The cornea is an optically transparent tissue that conveys images to the back of the eye. It includes avascular tissue to which nutrients and oxygen are supplied via bathing with lacrimal fluid and aqueous humour as well as from blood vessels that line the junction between the cornea and sclera. The cornea includes one pathway for the permeation of drugs into the eye. Other anatomical tissue structures associated with the eye include the lacrimal drainage system, which includes a secretory system, a distributive system and an excretory system. The secretory system comprises secretors that are stimulated by blinking and temperature change due to tear evaporation and reflex secretors that have an efferent parasympathetic nerve supply and secrete tears in response to physical or emotional stimulation. The distributive system includes the eyelids and the tear meniscus around the lid edges of an open eye, which spread tears over the ocular surface by blinking, thus reducing dry areas from developing.

As used herein, the term "implant" refers to a structure that can be configured to contain or be impregnated with a drug, for example via a drug core or a drug matrix, such as those as disclosed in this patent document and in US Patent Publ. No. 2013/0053794; U.S. Pat. No. 8,333,726 and US Patent Publ. No. 2010/0274204, which is herein incorporated by reference in its entirety. The terms "implant," "plug," "punctal plug," and "punctal implant" are meant herein to refer to similar structures. Likewise, the terms "implant body" and "plug body" are meant herein to refer to similar structures. The implants described herein may be inserted into the punctum of a subject, or through the punctum into the canaliculus. The implant may be also comprise the drug core or drug matrix itself, which is configured for insertion into the punctum without being housed in a carrier such as a punctal implant occluder, for example having a polymeric component and a therapeutic agent(s) component with no additional structure surrounding the polymeric component and latanoprost or other intraocular pressure-reducing therapeutic agent(s) component.

As used herein, the term "punctum" refers to the orifice at the terminus of the lacrimal canaliculus, seen on the margins of the eyelids at the lateral extremity of the lacus lacrimalis. Puncta (plural of punctum) function to reabsorb tears produced by the lacrimal glands. The excretory part of the lacrimal drainage system includes, in flow order of drainage, the lacrimal puncta, the lacrimal canaliculi, the lacrimal sac and the lacrimal duct. From the lacrimal duct, tears and other flowable materials drain into a passage of the nasal system. The lacrimal canaliculi include an upper (superior) lacrimal canaliculus and a lower (inferior) lacrimal canaliculus, which respectively terminate in an upper and lower lacrimal punctum. The upper and lower punctum are slightly elevated at the medial end of a lid margin at the junction of the ciliary and lacrimal portions near a conjunctival sac. The upper and lower punctum are generally round or slightly ovoid openings surrounded by a connective ring of tissue. Each of the puncta leads into a vertical portion of their respective canaliculus before turning more horizontal at a canaliculus curvature to join one another at the entrance of the lacrimal sac. The canaliculi are generally tubular in shape and lined by stratified squamous epithelium surrounded by elastic tissue, which permits them to be dilated.

The terms "subject" and "patient" refer to animals such as mammals, including, but not limited to, primates (e.g., humans), cows, sheep, goats, horses, dogs, cats, rabbits, rats, mice and the like. In many embodiments, the subject or patient is a human.

Insertion Tools

FIGS. 7-13 illustrate exemplary embodiments of punctal plug static pin insertion tools of the invention. Turning to FIG. 7, an exemplary insertion tool 700 is shown engaged with an implant 760 of the invention through meeting of pin 702 and insertion of the lacrimal implants into a lacrimal punctum. The lacrimal implants include the exemplary embodiments disclosed below, variations thereof, or any similar structures.

FIG. 7 shows an insertion tool 700 comprising an inserter tip 701, a screw 703, a spring 704, and a handle 705. The inserter tip comprises a static pin 702 at the distal end that is configured for placement in bore 385 of the punctal plug 760. In embodiments, the insertion tool does not comprise a mechanism for moving the pin 702. The inserter tip 701 further comprises a proximal end that snaps or locks into a distal end of the handle 705. In embodiments, the snap or lock mechanism is a friction fit between the handle 705 and tip 701. In embodiments, the length of the inserter tip 701 is about 0.75 to 1.5 inches and the length of the inserter tip after attachment with the handle 705 is about 0.5 to 1.25 inches. In embodiments, the diameter of the inserter tip 701 varies and is tapered from its largest diameter of about 0.5 to 0.1 inches to the pin 702 at the distal end.

The handle 705 comprises a screw 703 and spring 704 internal to the handle at the distal end and a plunger 706 at the proximal end. The plunger and spring are configured to release or eject the inserter tip when the plunger is depressed. The length of the handle can vary and is configured to fit comfortably in the hand of a user. In embodiments, the length of the handle 705 is 3.75 to 5.5 inches, including the plunger 706 at the proximal end of the handle.

In embodiments, FIGS. 13-18 show various views of the inserter tip, the handle and a lacrimal implant that may be coupled to the static pin of the inserter tip. In embodiments, the inserter tip is manufactured and comprises biocompatible polymers. In embodiments, the inserter tip is molded, with no movable parts, that may be solid or substantially sold. The density of the material used to manufacture the inserter tip may vary and may be selected to enhance the interference or friction fit of the inserter tip to the handle. In embodiments, the handle is manufactured from the same or different material as the inserter tip. In exemplary embodiments, the inserter tip and handle and manufactured from and comprise different material or polymers.

Lacrimal Implants

FIGS. 3-6 illustrate exemplary embodiments of lacrimal implants of use in the methods of the invention. The exemplary implants are insertable through a lacrimal punctum 212, 214 and into its associated canaliculus 208, 210. Exemplary lacrimal implants of use in the present invention comprise a first member, a second member and a heel, such as the first member 305, the second member 310 and the third member or heel 330 depicted in FIG. 3A. Exemplary lacrimal implants further comprise a bore that is formed in the heel, for example, the bore 385 formed in the third member or heel 330 in FIG. 3A. In some embodiments, exemplary lacrimal implants further comprise a cavity 458 (e.g., lacrimal implants illustrated in FIG. 4A).

Referring to FIG. 3A, where a perspective view of an exemplary lacrimal implant 300 of use in the present methods is depicted, the first member 305 is characterized by a first axis A and the second member 310 is characterized by a second axis B.

The third member or heel 330 is configured to connect the first member 305 and the second member 310 at a first angle $\theta_1$, where $\theta_1$ is defined by the first axis A with respect to the second axis B. For instance, in FIG. 3A, the first angle $\theta_1$ refers to the angle originating at the first axis A and turning counterclockwise from the first axis A to the second axis B. In some embodiments, the first axis A and the second axis B are in the same plane and intersect each other. In some embodiments, the first axis A is in a plane other than the plane of the second axis B, and the first axis A and the second axis B do not intersect. In such embodiments, the first angle $\theta_1$ refers to the angle defined by a parallel line of the first axis A with respect to the second axis B. This parallel line of the first axis A lies in the same plane as the second axis and intersects with the second axis.

In some embodiments, the first angle $\theta_1$ is from about 30 degrees to about 150 degrees, from about 45 degrees to about 135 degrees, or from about 75 degrees to about 105 degrees. For example, in some embodiments, the first angle $\theta_1$ is approximately 90 degrees.

In some embodiments, the overall dimension of the implant along the first axis is from about 4 mm to about 8 mm. In an exemplary embodiment, the overall dimension along the first axis is about 5 mm to about 7 mm. In various embodiments, the overall dimension along the first axis is about 6.3 mm.

In various embodiments, the overall dimension along the second axis B is from about 1 mm to about 3 mm, e.g., from about 1.2 mm to about 1.9 mm.

In some embodiments, the overall dimension along the first axis is approximately 6.3 mm and the overall dimension along the second axis is approximately 1.2 mm. In various embodiments, the overall dimension along the first axis is approximately 6.3 mm and the overall dimension along the second axis is approximately 1.9 mm. In some embodiments, the overall dimension along the first axis is approximately 4.8 mm and the overall dimension along the second axis is approximately 1.9 mm.

First Member 305

Figure 1:
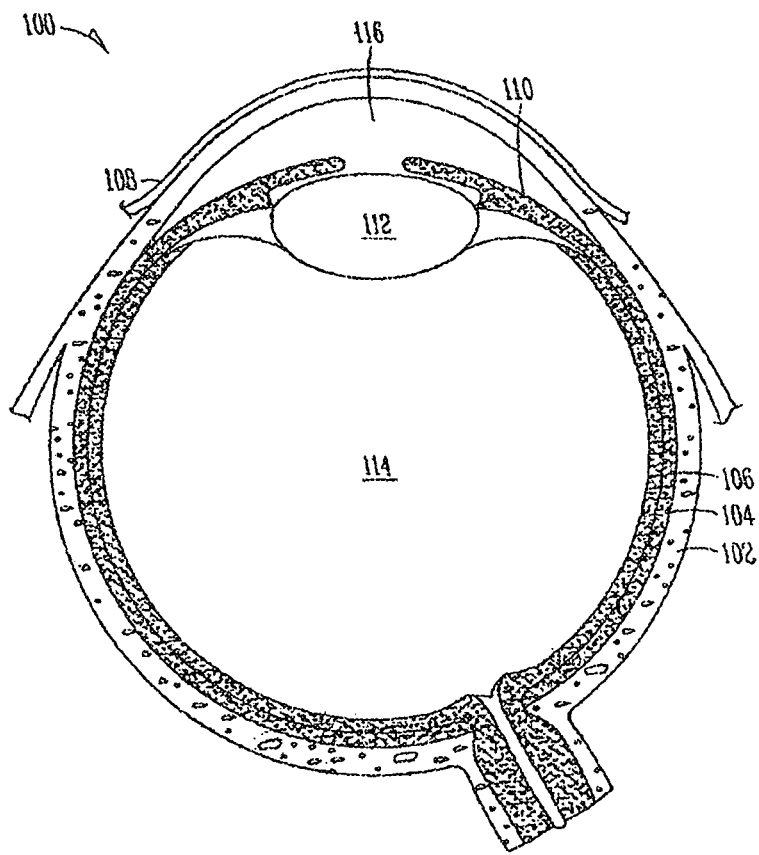
FIG. 1 illustrates an example of anatomical tissue structures associated with an eye, certain of these tissue structures providing a suitable environment in which a lacrimal implant can be used.
Figure 2:
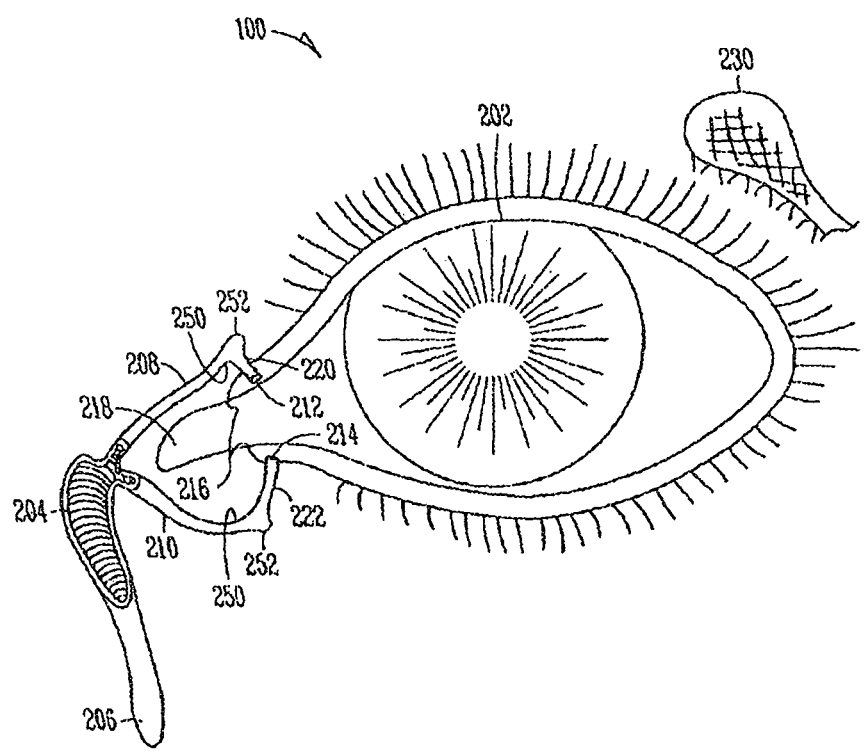
FIG. 2 illustrates another example of anatomical tissue structures associated with an eye, certain of these tissue structures providing a suitable environment in which a lacrimal implant can be used.

In some embodiments, the first member 305 is configured to extend into a canaliculus, while the second member 310 is configured to reside in the vertical portion 220, 222 of the canaliculus and to extend to the opening of, or out of the opening of, the associated puncta. When a lacrimal implant 300 of such configuration is inserted into a canaliculus, the intersection of the first axis A and the second axis B resides generally at a curvature of the canaliculus, such as the canaliculus curvature 250 in FIG. 2. In some embodiments, the first member 305 and the second member 310 are connected at the first angle, and that angle is at least about 45 degree, thereby forming an angled intersection between the first member and the second member. In various embodiments, when the lacrimal implant 300 is positioned in the lacrimal canaliculus, at least a portion of the angled intersection is biased against a canaliculus curvature of the lacrimal canaliculus. In this embodiment, the lacrimal implant 300 uses anatomical structures to facilitate the retention of the implanted lacrimal implant 300.

FIG. 3B depicts a side view of an exemplary lacrimal implant 300 of the invention. In some embodiments, the first member 305 includes an intermediate segment 315, a tip segment or tip 325, and a forward segment 320 in between the forward segment and tip segment. While the intermediate segment 315 is configured to be connected to the second member 310 by the third member or heel 330, the tip segment or tip 325 is configured to be inserted through a punctum prior to the other two segments of the first member 305 and prior to the other members of the lacrimal implant 300.

In some embodiments, the intermediate segment 315, the forward segment 320 and the tip segment or tip 325 are distinguishable from each other in general by their shapes. For example, in some embodiments, the intermediate segment 315 has a generally cylindrical shape with a diameter that is larger than the diameter of the tip segment or tip 325. In various embodiments, the forward segment 320 is tapered and has a conical shape, such that the forward segment 320 connects the intermediate segment 315 at one end and the tip segment or tip 325 at the other end. In some embodiments, the transition from the intermediate segment 315 to the forward segment 320 or the transition from the forward segment 320 to the tip segment or tip 325 is gradual and smooth such that no distinguishable edge exists at the transition.

In some embodiments, the intermediate segment 315 has a cylindrical shape. In various embodiments, the intermediate segment has a circular cross section, an elliptic cross section, or a polygonal cross section. The intermediate segment 315 is of any useful combination of length and diameter.

In some embodiments, the intermediate segment 315 has a diameter that is from about 0.4 mm to about 0.8 mm. For example, in some embodiments the diameter of the intermediate segment 315 is from about 0.53 mm to about 0.63 mm. In some embodiments, the intermediate segment 315 has a length along the first axis A that is from about 0.5 mm to about 3.5 mm. For example, in some embodiments the length of the intermediate segment 315 is from about 1 mm to about 2.8 mm.

In some embodiments, the tip segment or tip 325 is substantially a semi-sphere, or a portion of a semi-sphere. In exemplary embodiments, the semi-sphere, or portion therapy, has a radius that is from about 0.05 mm to about 0.3 mm. For example, in some embodiments, the radius of the tip segment or tip 325 is approximately 0.20 mm.

In some embodiments, the forward segment 320 has a conical configuration, tapering from the diameter of the intermediate segment 315 as it approaches the tip segment or tip 325. In some embodiments, the forward segment 320 is short and is tapered steeply, thus forming a wider taper angle. The forward segment 320 can also be long and tapered more gradually, thus forming a narrower taper angle. The tapering angle $\theta_3$ is illustrated in FIG. 3E. In some embodiments, the tapering angle $\theta_3$ is from about 2° to about 10°. For example, in some embodiments the tapering angle $\theta_3$ is from about 3.8° to about 7.8°. In some embodiments, $\theta_3$ is about 7.8°. In some embodiments, the forward segment 320 has a length along the first axis A that is from about 1 mm to about 5 mm. For example, in some embodiments the length of forward segment 320 is from about 1.7 mm to about 3.5 mm.

Second Member 310

Referring to FIG. 3B, in some embodiments of implants of use in the present method, the second member 310 includes an upright segment 335 that extends from the third member or heel 330 generally along the direction of the second axis B. In various embodiments, the second member 310 further includes a head segment 340 that attaches to the upright segment 335 at an end opposite to the third member or heel 330. In some embodiments, the second member 310 is configured such that the upright segment 335 resides in the vertical portion of the canaliculus while the head segment 340 contacts the tissue surrounding the exterior of the punctum when the lacrimal implant 300 is positioned in the lacrimal canaliculus. In an exemplary embodiment, illustrated in FIGS. 3A-3F, the upright segment 335 has a cylindrical shape and the head segment 340 has an oval or oblong configuration. However, it will be appreciated that any other suitable shapes or configurations can be used and are within the scope of the present invention. For example, in various embodiments, the upright segment 335 is configured to be a conical; the head segment 340 is configured to have a circular, elliptical or polygonal cross section.

In some embodiments, the upright segment 335 has a characteristic diameter that is from about 0.7 mm to about 0.9 mm. For example, in some embodiments, the characteristic diameter of the upright segment 335 is about 0.8 mm.

In some embodiments, the upright segment 335 has a length in the direction of the second axis B that is from about 0.7 mm to about 1.5 mm. For example, in some embodiments the length of upright segment 335 along the direction of the second axis B is about 0.9 mm.

Generally, the head segment 340 has a cross section characterized by a minor axis and a major axis. The minor axis and the major axis refer to the shortest characteristic diameter and the longest characteristic diameter of the cross section, respectively. As such, the minor axis is equal to or less than the major axis. For instance, in some embodiments where the head segment 340 has a circular cross section, the minor axis and the major axis are of equal length. In various embodiments, the head segment 340 has an oval or oblong cross section, and the minor axis is shorter than the major axis. In some embodiments, the head segment 340 is elongated in a direction that is parallel to the first axis A. The major axis indicates the extension of the first member 305 and facilitates positioning of the lacrimal implant 300 in the punctum and canaliculus. In some embodiments, the major axis is from about 1.5 mm to about 2.5 mm. In various embodiments, the minor axis is from about 1 mm to about 1.5 mm. For example, in some embodiments, the major axis and the minor axis head segment 340 are approximately 1.9 mm and 1.3 mm respectively. In some embodiments, the head segment 340 has a thickness in the direction of the second axis that is from about 0.2 mm to about 0.4 mm. For example, in some embodiments, the thickness of the head segment 340 in the direction of the second axis is approximately 0.3 mm.

Referring still to FIG. 3B, exemplary head segment 340 comprises an under-surface 350 facing towards the third member or heel 330 and an outer-surface 355 that faces away from the third member or heel 330. Exemplary head segment 340 further comprises an edge surface 345 that couples the under-surface 350 and the outer-surface 355. The distance between the under-surface 350 and the outer-surface 355 can be readily varied. In some embodiments, the distance is from about 0.2 mm to about 0.4 mm.

In some embodiments, the outer-surface 355 is smaller than the under-surface 350 and is substantially flat. In various embodiments, the edge surface 345 is tapered, curved, angular, or multifaceted. In some embodiments, the edge surface 345 has a radius of curvature that is from about 0.2 mm to about 0.7 mm. In some embodiments, the under-surface 350 is in general flat and is configured to contact the exterior tissue surrounding the punctum when the lacrimal implant 300 is positioned in the lacrimal canaliculus.

Third Member or Heel 330

In some embodiments, the third member or heel 330 includes an upper surface 360 a lower surface 365 and side surfaces 370. In the illustrated embodiments, the bore 385 extends from the upper surface 360 into the third member or heel 330. In some embodiments, the upper surface 360 and the lower surface 365 are substantially flat and separated from each other by a distance. Such distance is readily variable and is typically about 0.3 mm to about 0.7 mm. For instance, in some embodiments, the upper surface 360 and the lower surface 365 are separated by a distance that is from about 0.4 mm to 0.6 mm (e.g., about 0.53 mm). In some embodiments, the upper surface 360 extends beyond the intersection with the second member 310. In some embodiments, the upper surface 360 extends beyond the intersection with the second member 310 for a distance that is from about 0.3 to about 0.6 mm. The upper surface 360 can also be joined with the side surfaces 370. In various embodiments, upper surface 360 and side surfaces 370 are joined by a curved intersection 380. In some embodiments, the curved intersection 380 has a radius of curvature that is from about 0.04 mm to about 0.08 mm.

Referring now to FIGS. 3D and 3F, in some embodiments, the third member or heel 330 includes a heel connecting segment 375 configured to couple the third member or heel 330 to the first member 305 or to the intermediate segment 315 of the first member 305. The heel connecting segment 375 is of readily variable shape, including flat or curved structures. In FIG. 3F, a width of the heel connecting segment 375 in the direction of the second axis B varies along the direction of the first axis A. For example, the heel connecting segment 375 has a smaller width at or near the side surfaces 370 than the diameter of the intermediate segment 315 of the first member 305. In some embodiments, at or near the intersection with the intermediate segment 315, the heel connecting segment 375 increases the width and thus forms a notch as depicted in FIG. 3F. It will be appreciated that the notch can be either deeper or shallower along both the first axis A and the second axis B before it meets the first member 305 or the second member 310.

A notch is not a required feature in the implants of the present invention. In some embodiments, the heel connecting segment 375 has the same dimension as the diameter of the intermediate segment 315. For example, the thickness of the third member or heel 330 along the second axis B is equal to the diameter of the intermediate segment 315 of the first member 305. For example, in some embodiments, both the thickness of the third member or heel 330 in the direction of the second axis B and the diameter of the intermediate segment 315 are from about 0.53 mm to about 0.63 mm. In such configurations, the third member or heel 330 couples with the intermediate segment 315 without forming a notch, as illustrated by the alternative heel connecting segment 675 in FIG. 6.

By way of illustration, the third member or heel 330 depicted in FIGS. 3A-3F is substantially parallel to the first axis A of the first member 305. It would be appreciated that this is unnecessary. In some embodiments, the third member or heel 330 can form an angle with relation to the first axis A.

Bore 385

Exemplary structures of the bore 385 are detailed in FIGS. 3E and 3F, where a cross sectional view and a partial enlarged cross-sectional view of the lacrimal implant 300 are provided. The bore 385 is configured to receive a tip or other protrusion of an external insertion tool for facilitating insertion of the lacrimal implant 300 into a lacrimal punctum. The configuration, including size, shape, angle ($\theta_2$) and position of the bore in the heel are readily adjustable to facilitate the mating of the insertion tool with the bore, the flexibility of the heel, or the retention of the lacrimal implants. Depending on the purpose or use of the implant and the materials used for making the heel, the characteristics of the bore noted above are readily varied. Configurations of the bore 385 disclosed herein are illustrative and any other suitable configurations are within the scope of the present invention.

In FIG. 3F, an exemplary bore 385 is characterized by a third axis C and a second angle $\theta_2$ that is defined by the first axis with respect to the third axis A in a similar way as the first angle $\theta_1$. In some embodiments, the second angle $\theta_2$ is from about 15° to about 90°. For example, in some embodiments, the second angle $\theta_2$ is about 45°.

In some embodiments, the bore 385 has a depth along the direction of the third axis C that is from about 0.3 mm to about 0.7 mm. For example, in some embodiments the depth of the bore 385 is approximately 0.4 mm and in some embodiments, is approximately 0.6 mm. The bore 385 may include a bore shaft 390 that is generally cylindrical, with a circular, elliptical, oval, or polygonal cross section. The bore 385 may further include a bore tip 395 at which the bore shaft 390 terminates. An exemplary bore tip 395 generally has a semispherical configuration. In some embodiments, the bore shaft 390 has a characteristic diameter that is from about 0.1 mm to about 0.3 mm. In some embodiments, the characteristic diameter of the bore is approximately 0.17 mm. As will be appreciated, the shapes, sizes, orientations disclosed in the present application are illustrative, and any other suitable shapes, sizes, or orientations are within the scope of the present application. In addition, it will be appreciated that the opening of the bore can be positioned closer to the second member or closer to the edge of the heel.

Cavity 458

Figure 4A:
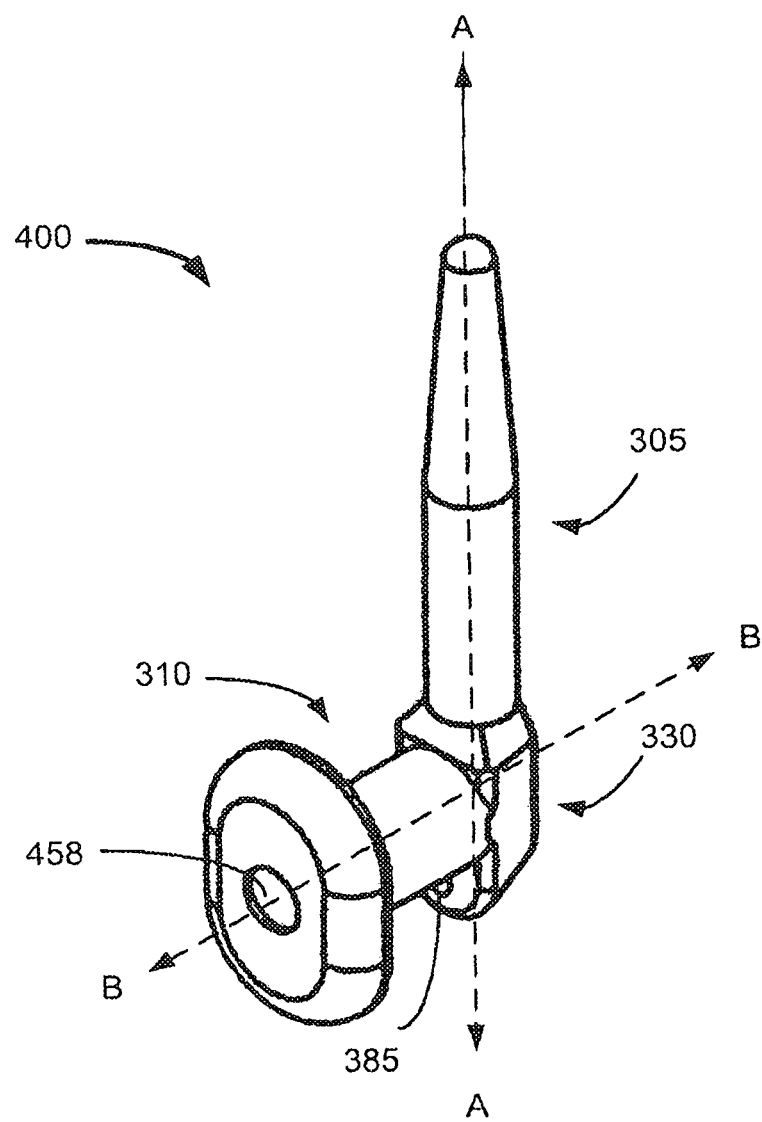
FIG. 4A provides a perspective view of an implant in accordance with an embodiment of the present invention.
Figures 4B, 4C:
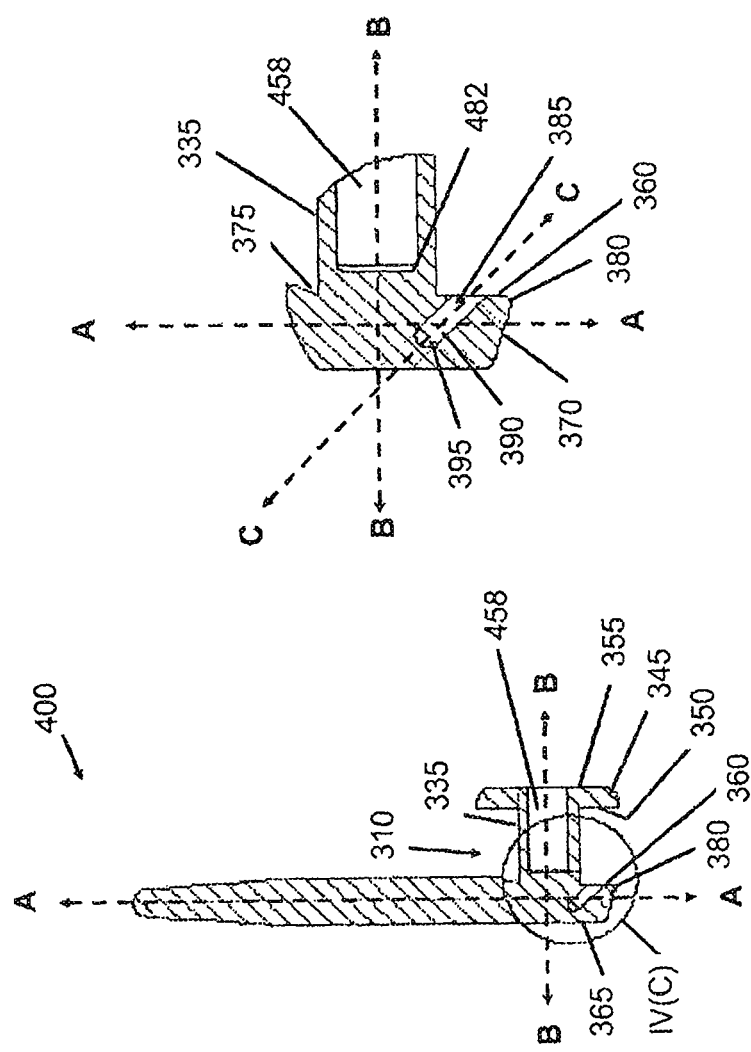
FIG. 4B is a cross-sectional view depicting an implant having a cavity formed in the second member, in accordance with an embodiment of the present invention.
FIG. 4C is a partially enlarged view taken about circle IV(C) of FIG. 4B depicting a cavity in the second member and a bore in the third member of an implant, in accordance with an embodiment of the present invention.

FIG. 4A-4C illustrates an exemplary lacrimal implant 400 that is insertable through a lacrimal punctum 212, 214 and into its associated canaliculus 208, 210. In FIG. 4A, the lacrimal implant 400 comprises a cavity 458 that is configured to house a therapeutic agent core or other materials for release into an eye or surrounding tissues for treatment of various ocular, sinus or other diseases.

In the illustrated exemplary embodiment, the cavity 458 is formed in the head segment 340 and has an opening through the outer-surface 355. The cavity 458 can be shallow such that it stays within the head segment 340. The cavity 458 can be also deeper and extend beyond the head segment 340 and into the upright segment 335. Illustrated exemplary cavity 458 is in general substantially cylindrical with a circular cross section. Any other suitable configuration is within the scope of the present application. For example, in some embodiments, the cavity 458 has a truncated spherical configuration, or has a cylindrical configuration with an oblong or a polygonal cross section.

In some embodiments, the cavity 458 has a depth in the direction of the second axis B that is about from 0.2 mm to about 1.4 mm. For example, in some embodiments, the depth of the cavity 458 is approximately 1.2 mm. In some embodiments, the cavity 458 has a diameter that is from about 0.3 mm to about 0.7 mm. For example, in some embodiments the diameter of the cavity 458 is from about 0.42 mm to about 0.55 mm. In an exemplary embodiment, the cavity 458 extends into the upright segment 335, and the diameter of the cavity 458 is smaller than the diameter of the upright segment 335.

Referring to FIG. 4C, the cavity 458 includes a bottom 482. In various embodiments, the bottom 482 is rounded. In various embodiments, the rounded bottom has a radius of curvature that is from about 0.03 mm to about 0.07 mm.

Figure 5:
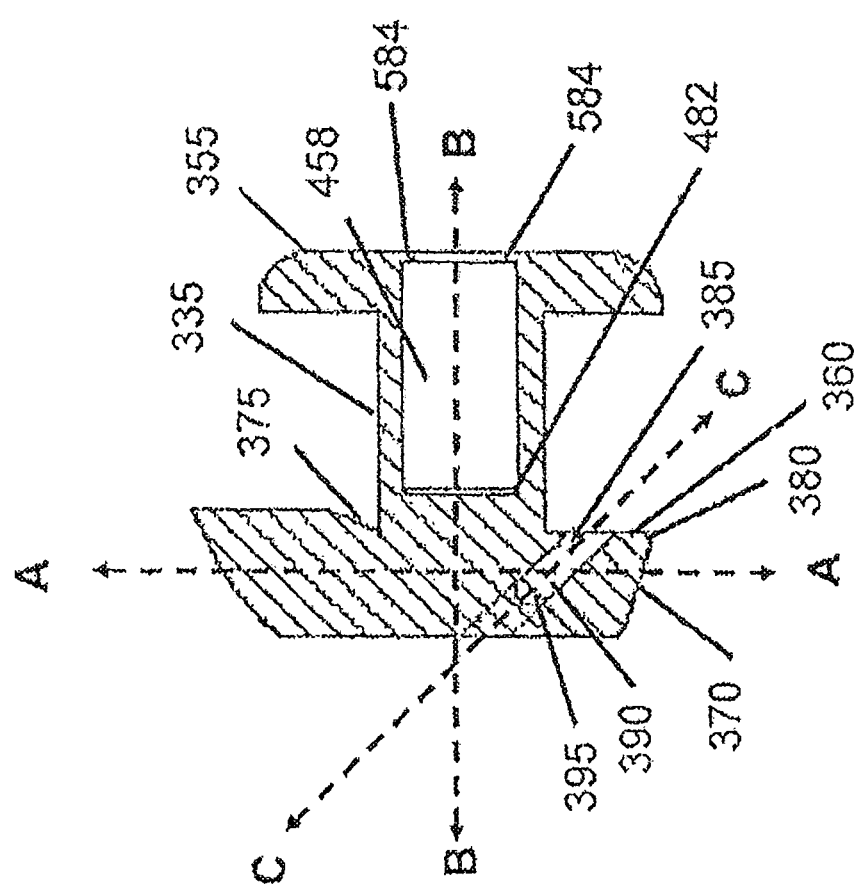
FIG. 5 provides a partial cross-sectional view of an implant in accordance with one embodiment of the present invention.
Figure 6:
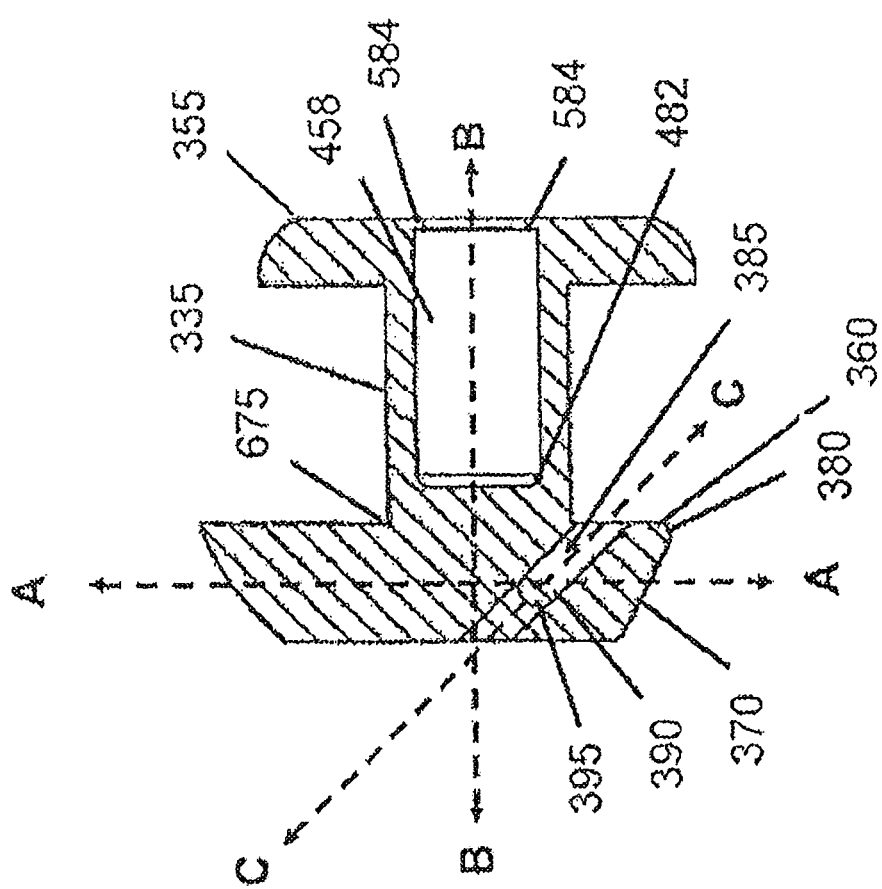
FIG. 6 provides a partial cross-section view of an implant in accordance with another embodiment of the present invention.

FIG. 5 depicts exemplary configurations of the cavity 458. In FIG. 5, the cavity 458 includes a lip 584 or other retaining structure positioned at the opening of the cavity 458. The lip 584 or the other retaining structure are optionally configured to partially enclose the cavity 458, e.g, prevent a therapeutic agent core or other materials from moving out of the cavity 458. In some embodiments, the lip 584 is a square cross-sectional annulus that extends down from the outer-surface 355 into the cavity 458 and extends inwardly towards the center of the opening of the cavity 458. In some embodiments, the lip 584 is of a tab configuration and includes a plurality of spaced lips that extend inwardly into the opening of the cavity 458. The lip 584 may extend downwardly from about 0.02 mm to about 0.1 mm and inwardly from about 0.02 mm to about 0.1 mm. For example, in some embodiments, the lip 584 extends about 0.05 mm downwardly or inwardly.

Formation of Lacrimal Implants

Exemplary lacrimal implants of use in methods of the present invention are made of various materials including plastic, rubber, polymer, or composite. Exemplary lacrimal implants of the present invention formed from one or more material including plastic, rubber, polymer, composites, or other appropriate materials. In some embodiments, the lacrimal implants are formed from liquid silicone rubber. For instance, in exemplary embodiments, lacrimal implants are formed from a material marketed as NuSil 4840 liquid silicone rubber, NuSil 4870, or a mixture including such a liquid silicone rubber. Examples of such a mixture include a material marketed as 6-4800, which comprises NuSil 4840 with from about 1% to about 5%, e.g., from about 2% to about 4% of 6-4800.

In some embodiments, the lacrimal implant is formed from biodegradable materials, for instance, biodegradable elastic materials including cross-linked polymers, such as poly (vinyl alcohol). In some embodiments, the lacrimal implant can comprise a co-polymer, such as silicone/polyurethane co-polymer, silicone/urethane, silicone/poly (ethylene glycol) (PEG), and silicone/2hydroxyethyl methacrylate (HEMA). As discussed in commonly-owned Utkhede et al., U.S. patent application Ser. No. 12/231,986, entitled "DRUG CORES FOR SUSTAINED RELEASE OF THERAPEUTIC AGENTS," filed Sep. 5, 2008, which is herein incorporated by reference in its entirety, urethane-based polymer and copolymer materials allow for a variety of processing methods and bond well to one another.

The hardness of the material is selected to facilitate or alter the retention of the lacrimal implant within the lacrimal punctum and its associated canaliculus. Accordingly, in some embodiments, a material having a durometer rating of from about 20D to about 80D, e.g., about 30D to about 70D, e.g., from about 40D to about 60D is of use to adjust parameters such as patient comfort and retention. For example, in some embodiments, the durometer rating of the material used to form the lacrimal implants is approximately 40D. Materials other than those exemplified above providing a durometer rating for the lacrimal implants within the stated ranges, and particularly that is about 40D are also of use. In some embodiments, a harder material or softer material is utilized for the entire lacrimal implant or for portions thereof. In such case, the lacrimal implants are formed from the materials that provide a durometer rating of about 70D.

In some embodiments, the lacrimal implants of use in the present methods are formed of multiple materials, where certain members or portions of the lacrimal implants are formed with materials having different properties. For example, in some embodiments the first member 305 is formed of a harder durometer rated material while the second member 310 is formed of a softer durometer rated material. In some embodiments, the first member 305 is formed of a softer durometer rated material while the second member 310 is formed of a harder durometer rated material. In some embodiments, the third member or heel 330 is formed of a harder durometer rated material than one or more parts of the remainder of the second member 310. In various embodiments, the third member or heel 330 is formed of a softer durometer rated material than the remainder of the second member 310.

Exemplary implants of use in the invention can be formed by methods known in the art, including, but not limited to, machining a blank to the desired shape and size and molding the material forming the implant.

The implant can be one of any number of different designs that releases latanoprost or other intraocular pressure-reducing therapeutic agent(s) for a sustained period of time. The disclosures of the following patent documents, which describe example implant structure or processing embodiments for use in the methods of embodiments of the current invention and methods of making those implants, are incorporated herein by reference in their entirety: U.S. Application Ser. No. 60/871,864 (filed Dec. 26, 2006 and entitled Nasolacrimal Drainage System Implants for Drug Therapy); U.S. application Ser. No. 11/695,537 (filed Apr. 2, 2007 and entitled Drug Delivery Methods, Structures, and Compositions for Nasolacrimal System); U.S. U.S. application Ser. No. 12/332,219 (filed Dec. 10, 2008 and entitled Drug Delivery Methods, Structures, and Compositions for Nasolacrimal System); U.S. Application Ser. No. 60/787,775 (filed Mar. 31, 2006 and entitled Nasolacrimal Drainage System Implants for Drug Therapy); U.S. application Ser. No. 11/695,545 (filed Apr. 2, 2007 and entitled Nasolacrimal Drainage System Implants for Drug Therapy); U.S. Application Ser. No. 60/585,287 (filed Jul. 2, 2004 and entitled Treatment Medium Delivery Device and Methods for Delivery of Such Treatment Mediums to the Eye Using Such a Delivery Device); U.S. application Ser. No. 11/571,147 (filed Dec. 21, 2006 and entitled Treatment Medium Delivery Device and Methods for Delivery of Such Treatment Mediums to the Eye Using Such a Delivery Device); U.S. Application Ser. No. 60/970,696 (filed Sep. 7, 2007 and entitled Expandable Nasolacrimal Drainage System Implants); U.S. Application Ser. No. 60/974,367 (filed Sep. 21, 2007 and entitled Expandable Nasolacrimal Drainage System Implants); U.S. Application Ser. No. 60/970,699 (filed Sep. 7, 2007 and entitled Manufacture of Drug Cores for Sustained Release of Therapeutic Agents); U.S. Application Ser. No. 60/970,709 (filed Sep. 7, 2007 and entitled Nasolacrimal Drainage System Implants for Drug Delivery); U.S. Application Ser. No. 60/970,720 (filed Sep. 7, 2007 and entitled Manufacture of Expandable Nasolacrimal Drainage System Implants); U.S. Application Ser. No. 60/970,755 (filed Sep. 7, 2007 and entitled Prostaglandin Analogues for Implant Devices and Methods); U.S. Application Ser. No. 60/970,820 (filed Sep. 7, 2007 and entitled Multiple Drug Delivery Systems and Combinations of Drugs with Punctal Implants); U.S. Application Ser. No. 61/066,223 (filed Feb. 18, 2008 and entitled Lacrimal Implants and Related Methods); U.S. Application Ser. No. 61/049,347 (filed Apr. 30, 2008 and entitled Lacrimal Implants and Related Methods); U.S. Application Ser. No. 61/033,211 (filed Mar. 3, 2008 and entitled Lacrimal Implants and Related Methods); U.S. Application Ser. No. 61/049,360 (filed Apr. 30, 2008 and entitled Lacrimal Implants and Related Methods); U.S. Application Ser. No. 61/052,595 (filed May 12, 2008 and entitled Lacrimal Implants and Related Methods); U.S. Application Ser. No. 61/075,309 (filed Jun. 24, 2008 and entitled Lacrimal Implants and Related Methods); U.S. Application Ser. No. 61/154,693 (filed Feb. 23, 2009 and entitled Lacrimal Implants and Related Methods); U.S. Application Ser. No. 61/209,036 (filed Mar. 2, 2009 and entitled Lacrimal Implants and Related Methods); U.S. Application Ser. No. 61/209,630 (filed Mar. 9, 2009 and entitled Lacrimal Implants and Related Methods); U.S. Application Ser. No. 61/036,816 (filed Mar. 14, 2008 and entitled Lacrimal Implants and Related Methods); U.S. Application Ser. No. 61/271,862 (filed Jul. 27, 2009 and entitled Lacrimal Implants and Related Methods); U.S. Application Ser. No. 61/252,057 (filed Oct. 15, 2009 and entitled Lacrimal Implants and Related Methods); U.S. application Ser. No. 12/710,855 (filed Feb. 23, 2010 and entitled Lacrimal Implants and Related Methods); U.S. Application Ser. No. 60/871,867 (filed Dec. 26, 2006 and entitled Drug Delivery Implants for Inhibition of Optical Defects); U.S. application Ser. No. 12/521,543 (filed Dec. 31, 2009 and entitled Drug Delivery Implants for Inhibition of Optical Defects); U.S. Application Ser. No. 61/052,068 (filed May 9, 2008 and entitled Sustained Release Delivery of Latanoprost to Treat Glaucoma); U.S. Application Ser. No. 61/052,113 (filed May 9, 2008 and entitled Sustained Release Delivery of Latanoprost to Treat Glaucoma); U.S. Application Ser. No. 61/108,777 (filed Oct. 27, 2008 and entitled Sustained Release Delivery of Latanoprost to Treat Glaucoma); U.S. application Ser. No. 12/463,279 (filed May 8, 2009 and entitled Sustained Release Delivery of Active Agents to Treat Glaucoma and Ocular Hypertension); U.S. Application Ser. No. 61/049,337 (filed Apr. 30, 2008 and entitled Lacrimal Implants and Related Methods); U.S. application Ser. No. 12/432,553 (filed Apr. 29, 2009 and entitled Composite Lacrimal Insert and Related Methods); U.S. Application Ser. No. 61/049,317 (filed Apr. 30, 2008 and entitled Drug-Releasing Polyurethane Lacrimal Insert); U.S. application Ser. No. 12/378,710 (filed Feb. 17, 2009 and entitled Lacrimal Implants and Related Methods); U.S.

Application Ser. No. 61/075,284 (filed Jun. 24, 2008 and entitled Combination Treatment of Glaucoma); U.S. application Ser. No. 12/490,923 (filed Jun. 24, 2009 and entitled Combination Treatment of Glaucoma); U.S. Application Ser. No. 61/134,271 (filed Jul. 8, 2008 and entitled Lacrimal Implant Body Including Comforting Agent); U.S. application Ser. No. 12/499,605 (filed Jul. 8, 2009 and entitled Lacrimal Implant Body Including Comforting Agent); U.S. Application Ser. No. 61/057,246 (filed May 30, 2008 and entitled Surface Treatment of Implants and Related Methods); U.S. Application Ser. No. 61/132,927 (filed Jun. 24, 2008 and entitled Surface Treated Implantable Articles and Related Methods); U.S. application Ser. No. 12/283,002 (filed Sep. 5, 2008 and entitled Surface Treated Implantable Articles and Related Methods); U.S. application Ser. No. 12/231,989 (filed Sep. 5, 2008 and entitled Lacrimal Implants and Related Methods); U.S. Application Ser. No. 61/049,317 (filed Apr. 30, 2008 and entitled Drug-Releasing Polyurethane Lacrimal Insert); U.S. application Ser. No. 12/231,986 (filed Sep. 5, 2008 and entitled Drug Cores for Sustained Release of Therapeutic Agents); U.S. Application Ser. No. 61/050,901 (filed May 6, 2008 and entitled Punctum Plug Detection); U.S. application Ser. No. 12/231,987 (filed Sep. 5, 2008 and entitled Lacrimal Implant Detection); U.S. Application Ser. No. 61/146,860 (filed Jan. 23, 2009 and entitled Sustained Release Delivery of One or More Anti-Glaucoma Agents); U.S. Application Ser. No. 61/152,909 (filed Feb. 16, 2009 and entitled Sustained Release Delivery of One or More Anti-Glaucoma Agents); U.S. Application Ser. No. 61/228,894 (filed Jul. 27, 2009 and entitled Sustained Release Delivery of One or More Anti-Glaucoma Agents); U.S. Application Ser. No. 61/277,000 (filed Sep. 18, 2009 and entitled Drug Cores for Sustained Ocular Release of Therapeutic Agents); U.S. application Ser. No. 12/692,452 (filed Jan. 22, 2010 and entitled Sustained Release Delivery of One or More Agents); U.S. Application Ser. No. 61/283,100 (filed Nov. 27, 2009 and entitled Lacrimal Implants Including Split and Insertable Drug Core); International Application Serial No. PCT/US2010/058129 (filed Nov. 26, 2010, published as WO 2011/066479 and entitled Lacrimal Implants Including Split and Insertable Drug Core); U.S. Application Ser. No. 61/139,456 (filed Dec. 19, 2008 and entitled Substance Delivering Punctum Implants and Methods); U.S. application Ser. No. 12/643,502 (filed Dec. 21, 2009 and entitled Substance Delivering Punctum Implants and Methods); U.S. application Ser. No. 10/825,047 (filed Apr. 15, 2004 and entitled Drug Delivery via Punctal Plug); U.S. application Ser. No. 12/604,202 (filed Oct. 22, 2009 and entitled Drug Delivery via Ocular Implant); International Application Serial No. PCT/US2005/023848 (filed Jul. 1, 2005, published as WO 2006/014434 and entitled Treatment Medium Delivery Device and Methods for Delivery); International Application Serial No. PCT/US2007/065792 (filed Apr. 2, 2007, published as WO 2007/115261 and entitled Drug Delivery Methods, Structures, and Compositions for Nasolacrimal System); and International Application Serial No. PCT/US2007/065789 (filed Apr. 2, 2007, published as WO 2007/115259 and entitled Nasolacrimal Drainage System Implants for Drug Therapy).

Retention

In various embodiments of the methods of the invention, an implant including a retention structure is employed to retain the implant in the punctum or canaliculus. The retention structure is attached to or integral with the implant body. The retention structure comprises an appropriate material that is sized and shaped so that the implant can be easily positioned in the desired tissue location, for example, the punctum or canaliculus. In some embodiments, the drug core may be attached to the retention structure via, at least in part, the sheath. In some embodiments, the retention structure comprises a hydrogel configured to expand when the retention structure is placed in the punctum. The retention structure can comprise an attachment member having an axially oriented surface. In some embodiments, expansion of the hydrogel can urge against the axially oriented surface to retain the hydrogel while the hydrogel is hydrated. In some embodiments, the attachment member can comprise at least one of a protrusion, a flange, a rim, or an opening through a portion of the retention structure. In some embodiments, the retention structure includes an implant body portion size and shape to substantially match an anatomy of the punctum and canaliculus.

The retention structure may have a size suitable to fit at least partially within the canalicular lumen. The retention structure can be expandable between a small profile configuration suitable for insertion and a large profile configuration to anchor the retention structure in the lumen, and the retention structure can be attached near the distal end of the drug core. In specific embodiments, the retention structure can slide along the drug core near the proximal end when the retention structure expands from the small profile configuration to the large profile configuration. A length of the retention structure along the drug core can be shorter in the large profile configuration than the small profile configuration.

In some embodiments, the retention structure is resiliently expandable. The small profile may have a cross section of no more than about 0.2 mm, and the large profile may have a cross section of no more than about 2.0 mm. The retention structure may comprise a tubular body having arms separated by slots. The retention structure can be disposed at least partially over the drug core.

In some embodiments, the retention structure is mechanically deployable and typically expands to a desired cross-sectional shape, for example with the retention structure comprising a super elastic shape memory alloy such as Nitinol™. Other materials in addition to Nitinol™ can be used, for example resilient metals or polymers, plastically deformable metals or polymers, shape memory polymers, and the like, to provide the desired expansion. In some embodiments polymers and coated fibers available from Biogeneral, Inc. of San Diego, Calif. may be used. Many metals such as stainless steels and non-shape memory alloys can be used and provide the desired expansion. This expansion capability permits the implant to fit in hollow tissue structures of varying sizes, for example canaliculae ranging from 0.3 mm to 1.2 mm (i.e. one size fits all). Although a single retention structure can be made to fit canaliculae from 0.3 to 1.2 mm across, a plurality of alternatively selectable retention structures can be used to fit this range if desired, for example a first retention structure for canaliculae from 0.3 to about 0.9 mm and a second retention structure for canaliculae from about 0.9 to 1.2 mm. The retention structure has a length appropriate to the anatomical structure to which the retention structure attaches, for example a length of about 3 mm for a retention structure positioned near the punctum of the canaliculus. For different anatomical structures, the length can be appropriate to provide adequate retention force, e.g. 1 mm to 15 mm lengths as appropriate.

Although the implant body may be attached to one end of the retention structure as described above, in many embodiments the other end of the retention structure is not attached to the implant body so that the retention structure can slide over the implant body including the sheath body and drug core while the retention structure expands. This sliding capability on one end is desirable as the retention structure may shrink in length as the retention structure expands in width to assume the desired cross sectional width. However, it should be noted that many embodiments may employ a sheath body that does not slide in relative to the core.

In many embodiments, the retention structure can be retrieved from tissue. A projection, for example a hook, a loop, or a ring, can extend from a portion of the implant body to facilitate removal of the retention structure.

In some embodiments the sheath and retention structure can comprise two parts.

The lacrimal implants of the present invention have exceptional retention properties, and are retained in the punctum and canaliculus for a period that is enhanced relative to a commercially available plug (FIG. 9) based upon the percentage of eyes in which an implant was implanted retaining the implant over a selected time period.

In an exemplary embodiment, the method of the invention uses a lacrimal implant configured to remain implanted in a punctum for at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In an exemplary embodiment, the lacrimal implant is configured to be retained by the puncta for the duration of the intended sustained release of the therapeutic agent. In various embodiments, the duration of the intended sustained release of the therapeutic agent is at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In various embodiments at least about 95%, at least about 90%, at least about 85% or at least about 80% of the implanted implants are retained for the duration of the intended controlled release of the therapeutic agent. In an exemplary embodiment, the implant is retained by the puncta for a length of time to show therapeutic efficacy.

In various embodiments, the present invention provides for the use of implants having structural features that enhance the retention of the implant in a punctum. Amongst other features, the heel of the present implant (e.g., 330) is configured to come to rest in the lacrimal canaliculus ampulla (e.g., 252), effectively locking the implant into place. However, the inventors have recognized that to prevent rotation and relative movement of the implanted device, which plays a role in the displacement of the device, a first member was needed to maintain the heel in the ampulla. Thus, the first member, e.g., 305, is configured to stabilize the punctal plug within the lacrimal canaliculus, prevent rotation and maintain positioning of the plug when the surrounding tissue moves.

Occlusive Element

In an exemplary embodiment, the methods of the invention use an implant having an occlusive element. An occlusive element can be mounted to and expandable with the retention structure to inhibit tear flow. An occlusive element may inhibit tear flow through the lumen, and the occlusive element may cover at least a portion of the retention structure to protect the lumen from the retention structure. The occlusive element comprises an appropriate material that is sized and shaped so that the implant can at least partially inhibit, even block, the flow of fluid through the hollow tissue structure, for example lacrimal fluid through the canaliculus. The occlusive material may be a thin walled membrane of a biocompatible material, for example silicone, that can expand and contract with the retention structure. The occlusive element is formed as a separate thin tube of material that is slid over the end of the retention structure and anchored to one end of the retention structure as described above. Alternatively, the occlusive element can be formed by dip coating the retention structure in a biocompatible polymer, for example silicone polymer. The thickness of the occlusive element can be in a range from about 0.01 mm to about 0.15 mm, and often from about 0.05 mm to 0.1 mm.

Therapeutic Agents and Therapeutic Agent Cores

Conventional drug delivery involving frequent periodic dosing is not ideal or practical in many instances. For example, with more toxic drugs, conventional periodic dosing can result in unfavorably high initial drug levels at the time of dosing, followed by low drug levels between doses often times below levels of therapeutic value. Likewise, conventional periodic dosing may not be practical or therapeutically effective in certain instances such as with pharmaceutical therapies targeting areas of the inner eye or brain in need of treatment such as the retina. Accordingly, in some embodiments, the lacrimal implant further includes one or more therapeutic agent within its structure. In various embodiments, the agent is dispersed throughout the device. In some embodiments, the agent is located at one or more distinct locations or zones of the device. In an exemplary embodiment, the therapeutic agent is located in a cavity of the device and the component holding the agent is referred to as a core.

In various embodiments, in which the agent is dispersed throughout the device, the rate and location of release of the agent is controlled by coating at least a component of the device with a material that is impermeable to the drug. In an exemplary embodiment, essentially the entire device is coated with the material with the exception of one or more gaps in the material through which the agent can elute into the eye or surrounding tissue. An exemplary coating is a Parylene coating (See, 2008/0181930, herein incorporated by reference).

In an exemplary embodiment, the lacrimal implant of the invention is configured as a sustained release device, releasing the incorporated therapeutic agent in a therapeutically effective manner, e.g., at a rate that provides a therapeutically effective dosage for at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In an exemplary embodiment, the lacrimal implant is configured to be retained by the puncta for the duration of the intended controlled release of the therapeutic agent. In various embodiments, the duration of the intended controlled release of the therapeutic agent is at least about 1 week, 2 weeks, 3 weeks, 4 weeks, 5 weeks, 6 weeks, 7 weeks, 8, weeks, 9 weeks 10 weeks, 11 weeks, or at least about 12 weeks or more. In various embodiments, at least 95% of the implanted implants are retained for the duration of the intended controlled release of the therapeutic agent. In an exemplary embodiment, the implant is retained by the puncta for a length of time to show therapeutic efficacy.

Therapeutic Agent Core

In an embodiment, the methods of the invention utilize an implant including a distinct therapeutic agent core or integrated drug or other agent disposed in at least one of the first member 305 or the second member 310 of the implant body, to provide a sustained release of a therapeutic agent. For instance, the drug core or integrated drug or other agent disposed may be disposed in the cavity 458 of the lacrimal implant 400 to provide a sustained drug or other therapeutic agent release.

An exemplary implant of use in the methods of the invention is configured to deliver a therapeutic agent to one or more of an eye, nasal passage or inner ear system. In various embodiments, the drug is delivered systemically to the subject through the eye. A therapeutic agent core can comprise one or more therapeutic agents, and in some examples, one or more matrix materials to provide sustained release of the drug or other agents.

In various embodiments, the therapeutic agent core is inserted into cavity 458.

In various examples, the distinct drug core or integrated drug or other agent includes at least about 20 micrograms, at least about 40 micrograms, at least about 45 micrograms, at least 80 micrograms, or at least 95 micrograms of a drug (e.g., latanoprost), such as is further discussed in commonly-owned Butuner et al., U.S. patent application Ser. No. 12/463,279, entitled "SUSTAINED RELEASE DELIVERY OF ACTIVE AGENTS TO TREAT GLAUCOMA AND OCULAR HYPERTENSION," filed May 8, 2009, and commonly-owned Utkhede, U.S. Patent Application No. 61/277,000, entitled "IMPROVED DRUG CORES FOR SUSTAINTED OCULAR RELEASE OF THERAPEUTIC AGENTS," filed Sep. 18, 2009, both of which are incorporated by reference in their entirety, including their descriptions of drug or other agent concentration.

The drug core can comprise one or more biocompatible materials capable of providing a sustained release of the one or more drugs or agents. The drug core can comprise a matrix including a substantially non-biodegradable silicone matrix with dissolvable inclusions of the drugs or agents located therein. The drug core can include other structures that provide sustained release of the drugs or agents, for example a biodegradable matrix, a porous drug core, a liquid drug core or a solid drug core. A matrix that includes the drugs or agents can be formed from either biodegradable or non-biodegradable polymers. In some examples, a non-biodegradable drug core can include silicone, acrylates, polyethylenes, polyurethane, polyurethane, hydrogel, polyester (e.g., DACRON™. from E.I. Du Pont de Nemours and Company, Wilmington, Del.), polypropylene, polytetrafluoroethylene (PTFE), expanded PTFE (ePTFE), polyether ether ketone (PEEK), nylon, extruded collagen, polymer foam, silicone rubber, polyethylene terephthalate, ultra high molecular weight polyethylene, polycarbonate urethane, polyurethane, polyimides, stainless steel, nickel-titanium alloy (e.g., Nitinol), titanium, stainless steel, cobalt-chrome alloy (e.g., ELGILOY™. from Elgin Specialty Metals, Elgin, Ill.; CONICHROME™. from Carpenter Metals Corp., Wyomissing, Pa.). In some examples, a biodegradable drug core can comprise one or more biodegradable polymers, such as protein, hydrogel, polyethylene oxides, polyglycolic acid (PGA), polylactic acid (PLA), poly(L-lactic acid) (PLLA), poly(L-glycolic acid) (PLGA), polyglycolide, poly-L-lactide, poly-D-lactide, poly(amino acids), polydioxanone, polycaprolactone, polygluconate, polylactic acid-polyethylene oxide copolymers, modified cellulose, collagen, polyorthoesters, polyhydroxybutyrate, polyanhydride, polyphosphoester, poly(alpha-hydroxy acid) and combinations thereof. In some examples, the drug core can comprise a hydrogel polymer.

Sheath Body

In an exemplary embodiment, the implant of use in the methods of the invention includes a therapeutic agent core which is encased in a sheath body. The sheath body can comprise appropriate shapes and materials to control the migration of latanoprost or other anti-glaucoma agent from the drug core. In some embodiments, the sheath body houses the drug core and can fit snugly against the core. The sheath body is made from a material that is substantially impermeable to the latanoprost or other anti-glaucoma agent so that the rate of migration of the agent may be largely controlled by the exposed surface area of the drug core that is not covered by the sheath body. In many embodiments, migration of the latanoprost or other anti-glaucoma agent through the sheath body can be about one tenth of the migration of latanoprost or other anti-glaucoma agent through the exposed surface of the drug core, or less, often being one hundredth or less. In other words, the migration of the latanoprost or other anti-glaucoma agent through the sheath body is at least about an order of magnitude less that the migration of latanoprost or other anti-glaucoma agent through the exposed surface of the drug core. Suitable sheath body materials include polyimide, polyethylene terephthalate (hereinafter "PET"). The sheath body has a thickness, as defined from the sheath surface adjacent the core to the opposing sheath surface away from the core, from about 0.00025" to about 0.0015". The total diameter of the sheath that extends across the core ranges from about 0.2 mm to about 1.2 mm. The core may be formed by dip coating the core in the sheath material. Alternatively or in combination, the sheath body can comprise a tube and the core introduced into the sheath, for example as a liquid or solid that can be slid, injected or extruded into the sheath body tube. The sheath body can also be dip coated around the core, for example dip coated around a pre-formed core.

The sheath body can be provided with additional features to facilitate clinical use of the implant. For example, the sheath may receive a drug core that is exchangeable while the implant body, retention structure and sheath body remain implanted in the subject. The sheath body is often rigidly attached to the retention structure as described above, and the core is exchangeable while the retention structure retains the sheath body. In specific embodiments, the sheath body can be provided with external protrusions that apply force to the sheath body when squeezed and eject the core from the sheath body. Another drug core can then be positioned in the sheath body. In many embodiments, the sheath body or retention structure may have a distinguishing feature, for example a distinguishing color, to show placement such that the placement of the sheath body or retention structure in the canaliculus or other body tissue structure can be readily detected by the subject. The retention element or sheath body may comprise at least one mark to indicate the depth of placement in the canaliculus such that the retention element or sheath body can be positioned to a desired depth in the canaliculus based on the at least one mark.

Therapeutic Agents

Generally, pharmaceutically active agents or drugs useful in the methods of the present invention can be any compound, composition of matter, or mixtures thereof that can be delivered from an implant, such as those described herein, to produce a beneficial and useful result to, for example, the eye, especially an agent effective in obtaining a desired local or systemic physiological or pharmacological effect.

Examples of such agents include, but are not limited to, anesthetics and pain killing agents such as lidocaine and related compounds, benzodiazepam and related compounds and the like; anti-cancer agents such as 5-fluorouracil, adriamycin and related compounds and the like; anti-fungal agents such as fluconazole and related compounds and the like; anti-viral agents such as trisodium phosphomonoformate, trifluorothymidine, acyclovir, ganciclovir, DDI, AZT and the like; cell transport/mobility impending agents such as colchicine, vincristine, cytochalasin B and related compounds and the like; antiglaucoma drugs (e.g. adrenergic agonists, adrenergic antagonists (beta blockers), carbonic anhydrase inhibitors (CAIs, systemic and topical), parasympathomimetics, prostaglandins and hypotensive lipids, and combinations thereof), antimicrobial agent (e.g., antibiotic, antiviral, antiparacytic, antifungal, etc.), a corticosteroid or other anti-inflammatory (e.g., an NSAID or other analgesic and pain management compounds), a decongestant (e.g., vasoconstrictor), an agent that prevents of modifies an allergic response (e.g., an antihistamine, cytokine inhibitor, leucotriene inhibitor, IgE inhibitor, immunomodulator), a mast cell stabilizer, cycloplegic, mydriatic or the like.

Other agents that can be incorporated into devices of use in the invention include antihypertensives; decongestants such as phenylephrine, naphazoline, tetrahydrazoline and the like; immunological response modifiers such as muramyl dipeptide and related compounds and the like; peptides and proteins such as cyclosporin, insulin, growth hormones, insulin related growth factor, heat shock proteins and related compounds and the like; steroidal compounds such as dexamethasone, prednisolone and related compounds and the like; low solubility steroids such as fluocinolone acetonide and related compounds and the like; carbonic anhydrase inhibitors; diagnostic agents; antiapoptosis agents; gene therapy agents; sequestering agents; reductants such as glutathione and the like; antipermeability agents; antisense compounds; antiproliferative agents; antibody conjugates; antidepressants; bloodflow enhancers; antiasthmatic drugs; antiparasiticagents; non-steroidal anti-inflammatory agents such as ibuprofen and the like; nutrients and vitamins: enzyme inhibitors: antioxidants; anticataract drugs; aldose reductase inhibitors; cytoprotectants; cytokines, cytokine inhibitors, and cytokin protectants; uv blockers; mast cell stabilizers; anti neovascular agents such as antiangiogenic agents, e.g., matrix metalloprotease inhibitors and the like.

Representative examples of additional pharmaceutically active agent for use herein include, but are not limited to, neuroprotectants such as nimodipine and related compounds and the like; antibiotics such as tetracycline, chlortetracycline, bacitracin, neomycin, polymyxin, gramicidin, oxytetracycline, chloramphenicol, gentamycin, erythromycin and the like; anti-infectives; antibacterials such as sulfonamides, sulfacetamide, sulfamethizole, sulfisoxazole; nitrofurazone, sodium propionate and the like; antiallergenics such as antazoline, methapyriline, chlorpheniramine, pyrilamine, prophenpyridamine and the like; anti-inflammatories such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triminolone and the like; miotics; anti-cholinesterase such as pilocarpine, eserine salicylate, carbachol, di-isopropyl fluorophosphate, phospholine iodine, demecarium bromide and the like; miotic agents; mydriatics such as atropine sulfate, cyclopentolate, homatropine, scopolamine, tropicamide, eucatropine, hydroxyamphetamine and the like; svmpathomimetics such as epinephrine and the like; and prodrugs such as, for example, those described in Design of Prodrugs, edited by Hans Bundgaard, Elsevier Scientific Publishing Co., Amsterdam, 1985. In addition to the foregoing agents, other agents suitable for treating, managing, or diagnosing conditions in a mammalian organism may be entrapped in the copolymer and administered using the drug delivery systems of the current invention. Once again, reference may be made to any standard pharmaceutical textbook such as, for example, Remington's Pharmaceutical Sciences for pharmaceutically active agents.

Any pharmaceutically acceptable form of the foregoing therapeutically active agent may be employed in the practice of the present invention, e.g., the free base; free acid; pharmaceutically acceptable salts, esters or amides thereof, e.g., acid additions salts such as the hydrochloride, hydrobromide, sulfate, bisulfate, acetate, oxalate, valerate, oleate, palmitate, stearate, laurate, borate, benzoate, lactate, phosphate, tosylate, mesylate, citrate, maleate, fumarate, succinate, tartrate, ascorbate, glucoheptonate, lactobionate, and lauryl sulfate salts and the like; alkali or alkaline earth metal salts such as the sodium, calcium, potassium and magnesium salts and the like; hydrates; enantiomers; isomers; stereoisomers; diastereoisomers; tautomers; polymorphs, mixtures thereof, prodrugs thereof or racemates or racemic mixtures thereof.

Additional agents that can be used with the present methods utilizing lacrimal implants include, but are not limited to, drugs that have been approved under Section 505 of the United States Federal Food, Drug, and Cosmetic Act or under the Public Health Service Act, some of which can be found at the U.S. Food and Drug Administration (FDA) website http://www.accessdatalda.gov/scripts/cder/drugsatfda/index. The present lacrimal implants can also be used with drugs listed in the Orange Book, either in paper or in electronic form, which can be found at the FDA Orange Book website (http://www.fda.gov/cder/ob/)), that has or records the same date as, earlier date than, or later date than, the filing date of this patent document. For example, these drugs can include, among others, dorzolamide, olopatadine, travoprost, bimatoprost, cyclosporin, brimonidine, moxifloxacin, tobramycin, brinzolamide, aciclovir timolol maleate, ketorolac tromethamine, prednisolone acetate, sodium hyaluronate, nepafenac, bromfenac, diclofenac, flurbiprofen, suprofenac, binoxan, patanol, dexamethasone/tobramycin combination, moxifloxacin, or acyclovir.

Further discussion of drugs or other agents can be found in commonly-owned U.S. Patent Application Publication No. 2009/0104248, U.S. Patent Application Publication No. 2010/0274204, and U.S. Patent Application Publication No. 2009/0105749, which are herein incorporated by reference in its entirety.

Actual dosage levels of the pharmaceutically active agent(s) in the drug delivery systems of use in the present invention may be varied to obtain an amount of the pharmaceutically active agent(s) that is effective to obtain a desired therapeutic response for a particular system and method of administration. The selected dosage level therefore depends upon such factors as, for example, the desired therapeutic effect, the route of administration, the desired duration of treatment, and other factors. The total daily dose of the pharmaceutically active agent(s) administered to a host in single or divided doses can vary widely depending upon a variety of factors including, for example, the body weight, general health, sex, diet, time and route of administration, rates of absorption and excretion, combination with other drugs, the severity of the particular condition being treated, etc. Generally, the amounts of pharmaceutically active agent(s) present in the drug delivery systems of the present invention can range from about 0.1% w/w to about 60% w/w and preferably from about 1% w/w to about 50% w/w.

Examples of diseases or disorders that can be treated according to the methods of the invention with above-listed agents include, but are not limited to, glaucoma, pre- and post-surgical ocular treatments, dry eye, anti-eye allergy, anti-infective, post-surgical inflammation or pain, respiration-related disorders, such as allergies, inner ear disorders, such as dizziness or migraines, or other systemic disorders, such as hypertension, cholesterol management, pulmonary disorders or immunological disorders. In some examples, the therapeutic agent can include a lubricant or a surfactant, for example a lubricant to treat dry eye. In other examples, the therapeutic agent can include an absorbent capable of absorbing tear from an eye.

Additional diseases treatable by a method of the invention include matrix controlled diffusion drug delivery systems of the present invention may be used in a broad range of therapeutic applications. The matrix controlled diffusion drug delivery systems of the present invention are particularly useful in the treatment of ophthalmic diseases, disorders and/or injuries. Representative examples of such ophthalmic diseases, disorders or injuries include, but are not limited to, diabetic retinopathy, glaucoma, macular degeneration, retinitis pigmentosa, retinal tears or holes, retinal-detachment, retinal ischemia, acute retinopathies associated with trauma, inflammatory mediated degeneration, post-surgical complications, damage associated with laser therapy including photodynamic therapy (PDT), surgical light induced iatrogenic retinopathy, drug-induced retinopathies, autosomal dominant optic atrophy, toxic/nutritional amblyopias; leber's hereditary optic neuropathy (LHOP), other mitochondrial diseases with ophthalmic manifestations or complications, angiogenesis; atypical RP; bardet-biedl syndrome; blue-cone monochromacy; cataracts; central areolar choroidal dystrophy; choroideremia; cone dystrophy; rod dystrophy; cone-rod dystrophy; rod-cone dystrophy; congenital stationary night blindness; cytomegalovirus retinitis; diabetic macular edema; dominant drusen; giant cell arteritis (GCA); goldmann-favre dystrophy; graves' ophthalmopathy; gyrate atrophy; hydroxychloroquine; iritis; juvenile retinoschisis; kearns-sayre syndrome; lawrence-moon bardet-biedl syndrome; leber congenital amaurosis; lupus-induced cotton wool spots; macular degeneration, dry form; macular degeneration, wet form; macular drusen; macular dystrophy; malattia leventinese; ocular histoplasmosis syndrome; oguchi disease; oxidative damage; proliferative vitreoretinopathy; refsum disease; retinitis punctata albescens; retinopathy of prematurity; rod monochromatism; RP and usher syndrome; scleritis; sector RP; sjogren-larsson syndrome; sorsby fundus dystrophy; stargardt disease and other retinal diseases.

The methods of the present invention can be administered to a mammal in need of treatment by way of a variety of routes. For example, drug delivery systems may be used by implantation within a portion of the body in need of localized drug delivery, e.g., the interior portion of an eye. However, the exemplary matrix controlled diffusion drug delivery systems may likewise be used in accordance with other surgical procedures known to those skilled in the field of ophthalmology. For example, the drug delivery systems can be administered to the region of the eye in need of treatment employing instruments known in the art, e.g., a flexible microcatheter system or cannula disclosed in U.S. Patent Application Publication No. 2002/0002362, or the intraretinal delivery and withdrawal systems disclosed in U.S. Pat. Nos. 5,273,530 and 5,409,457, the contents of each of which are incorporated by reference herein. The pharmaceutically active agent may be released from the drug delivery device over a sustained and extended period of time. Optionally, the drug release rate may also be controlled through the attachment of an inert diffusion barrier by way of, for example, surface treatment of the drug delivery device. The surface treatment may be applied through a variety of surface treatment techniques known in the art, e.g., oxidative plasma, evaporative deposition, dip coating or extrusion techniques.

The therapeutic agent can be present in the device in a formulation with a pharmaceutically acceptable carrier, e.g., excipients, suspending agents, diluents, fillers, salts, buffers, stabilizers, solubilizers, solvents, dispersion media, coatings, isotonic agents, and other materials known in the art. The pharmaceutical formulation optionally includes potentiators, complexing agents, targeting agents, stabilizing agents, cosolvents, pressurized gases, or solubilizing conjugates.

Exemplary excipients include sugars such as lactose, sucrose, mannitol, or sorbitol; cellulose preparations such as, maize starch, wheat starch, rice starch, potato starch, gelatin, gum tragacanth, methyl cellulose, hydroxypropyl-methylcellulose, sodium caroxymethylcellulose, and/or polyvinylpyrrolidone (PVP). Preferred excipients include lactose, gelatin, sodium carboxymethyl cellulose, and low molecular weight starch products.

Exemplary suspending agents that can serve as valve lubricants in pressurized pack inhaler systems are desirable. Such agents include oleic acid, simple carboxylic acid derivatives, and sorbitan trioleate.

Exemplary diluents include water, saline, phosphate-buffered citrate or saline solution, and mucolytic preparations. Other diluents that can be considered include alcohol, propylene glycol, and ethanol; these solvents or diluents are more common in oral aerosol formulations. Physiologically acceptable diluents that have a tonicity and pH compatible with the alveolar apparatus are desirable. Preferred diluents include isotonic saline, phosphate buffered isotonic solutions whose tonicity have been adjusted with sodium chloride or sucrose or dextrose or mannitol.

Exemplary fillers include glycerin, propylene glycol, ethanol in liquid or fluid preparations. Suitable fillers for dry powder inhalation systems include lactose, sucrose, dextrose, suitable amino acids, and derivatives of lactose. Preferred fillers include glycerin, propylene glycol, lactose and certain amino acids.

Exemplary salts include those that are physiologically compatible and provide the desired tonicity adjustment. Monovalent and divalent salts of strong or weak acids are desirable. Preferred salts include sodium chloride, sodium citrate, ascorbates, sodium phosphates.

Exemplary buffers include phosphate or citrate buffers or mixed buffer systems of low buffering capacity. Preferred buffers include phosphate or citrate buffers.

The Abstract is provided to comply with 37 C.F.R. § 1.72(b), to allow the reader to quickly ascertain the nature of the technical disclosure. It is submitted with the understanding that it will not be used to interpret or limit the scope or meaning of the claims.

What is claimed is:

1. A lacrimal implant insertion tool comprising:
   an inserter tip comprising a static pin at a distal end configured to be placed in a bore of a lacrimal implant and a mechanical coupling configured to receive a handle at a proximal end of the inserter tip; and,
   a handle coupled to the inserter tip at a distal end of the handle and a plunger at a proximal end of the handle, wherein the plunger is configured to release the inserter tip from the handle.

2. The insertion tool of claim 1, wherein the handle comprises a spring and a screw in a lumen of the handle and the proximal end of the inserter tip is configured to be coupled to the handle.

3. The insertion tool of claim 2, wherein the plunger is configured to slide within the lumen of the handle and release the inserter tip from the handle.

4. The insertion tool of claim 1, wherein the inserter tip and handle are coupled via a friction fit.

5. The insertion tool of claim 1, wherein the inserter tip comprises biocompatible polymers.

6. The insertion tool of claim 1, wherein the inserter tip is 0.75 to 1.5 inches in length.

7. The insertion tool of claim 1, wherein the inserter tip is 0.5 to 1.25 inches in length when the inserter tip and handle are coupled.

8. The insertion tool of claim 1, wherein the handle is 3.75 to 5.5 inches in length.

9. The insertion tool of claim 1, wherein the inserter tip is disposable.

10. A system for treatment of an eye comprising:
    an inserter tip comprising a static pin at a distal end configured to be placed in a bore of a lacrimal implant and a mechanical coupling configured to receive a handle at a proximal end of the inserter tip; and
    a lacrimal implant coupled to the static pin of the inserter tip.

11. The system of claim 10, further comprising a handle coupled to the inserter tip at a distal end of the handle and a plunger at a proximal end of the handle, wherein the plunger is configured to release the inserter tip from the handle.

12. The system of claim 11, wherein the inserter tip is 0.5 to 1.25 inches in length when the inserter tip and the handle are coupled.

13. The system of claim 11, wherein the handle is 3.75 to 5.5 inches in length.

14. The system of claim 10, wherein the handle comprises a spring and a screw in a lumen of the handle and the proximal end of the inserter tip is configured to be coupled to the handle.

15. The system of claim 10, wherein the plunger is configured to slide within the lumen of the handle and release the inserter tip from the handle.

16. The system of claim 10, wherein the inserter tip and handle are coupled via a friction fit.

17. The system of claim 10, wherein the inserter tip comprises biocompatible polymers.

18. The system of claim 10, wherein the inserter tip is 0.75 to 1.5 inches in length.

19. The system of claim 18, further comprising packaging.

20. The system of claim 10, wherein the inserter tip is disposable.

21. The system of claim 10, wherein the lacrimal implant comprises:
    a first member defining a first axis and having a first end along the first axis, wherein the first member is configured to extend into the canaliculus;
    a second member defining a second axis and having a second end along the second axis, wherein the second member is configured to reside in a vertical portion of the canaliculus and to extend to an opening of, or out of the opening of, an associate lacrimal punctum;
    a third member connecting the first end of the first member and the second end of the second member at a first angle to form an angled intersection; the third member comprises a bore defining a third axis and a second angle and having an upper surface;
    wherein the bore is configured to be accessible to the static pin of the inserter tip for facilitating insertion of the implant and extends from the upper surface into the third member; and further wherein the first angle is defined by the first axis with respect to the second axis and the second angle is defined by the first axis with respect to the third axis;
    wherein the first angle is from 30 degrees to 150 degrees;
    wherein the second angle is from 15 degrees to 90 degrees.

22. The system of claim 10, wherein the lacrimal implant comprises:
    a first member defining a first axis and having a first end along the first axis, wherein the first member is configured to extend into the canaliculus;
    a second member defining a second axis and having a second end along the second axis, wherein the second member is configured to reside in a vertical portion of the canaliculus and to extend to an opening of, or out of the opening of, an associate lacrimal punctum;
    a cavity that is configured to house a therapeutic agent core, wherein the cavity extends into the second member along the second axis;
    a third member connecting the first end of the first member and the second end of the second member at a first angle to form an angled intersection; the third member comprises a bore defining a third axis and a second angle and having an upper surface;
    wherein the bore is configured to be accessible to the static pin of the inserter tip for facilitating insertion of the implant and extends from the upper surface into the third member; and further wherein the first angle is defined by the first axis with respect to the second axis and the second angle is defined by the first axis with respect to the third axis;
    wherein the first angle is from 30 degrees to 150 degrees;
    wherein the second angle is from 15 degrees to 90 degrees.

23. A method for inserting a lacrimal implant using an insertion tool, comprising:
    coupling the system of claim 10 to a handle, wherein the handle is coupled to the inserter tip at a distal end of the handle and the handle comprises a plunger at a proximal end of the handle, wherein the plunger is configured to release the inserter tip from the handle, wherein the static pin is static relative to the inserter tip;
    placing the lacrimal implant in a punctum; and,
    de-coupling the inserter tip from the lacrimal implant wherein the static pin is released without mechanical force from the insertion tool.

24. The method of claim 23, further comprising ejecting the inserter tip from the handle by depressing the plunger on the proximal end of the handle.

25. The method of claim 23, wherein the handle comprises a spring and a screw in a lumen of the handle and the proximal end of the inserter tip is configured to couple the inserter tip and handle.

26. The method of claim 23, wherein the plunger is configured to slide within the lumen of the handle and release the inserter tip from the handle.

27. The method of claim 23, wherein the inserter tip and handle are coupled via a friction fit.

28. The method of claim 23, wherein the inserter tip comprises biocompatible polymers.

29. The method of claim 23, wherein the inserter tip is 0.75 to 1.5 inches in length.

30. The method of claim 23, wherein the system is removed from packaging after the handle is coupled to the inserter tip.

31. The method of claim 23, wherein the inserter tip is 0.5 to 1.25 inches in length when the inserter tip and the handle are coupled.

32. The method of claim 23, wherein the handle is 3.75 to 5.5 inches in length.

33. The method of claim 23, wherein the inserter tip is disposable.

34. The method of claim 23, wherein the handle is provided separately from the system.

35. The method of claim 23, wherein the lacrimal implant comprises:
- a first member defining a first axis and having a first end along the first axis, wherein the first member is configured to extend into the canaliculus;
- a second member defining a second axis and having a second end along the second axis, wherein the second member is configured to reside in a vertical portion of the canaliculus and to extend to an opening of, or out of the opening of, an associate lacrimal punctum;
- a third member connecting the first end of the first member and the second end of the second member at a first angle to form an angled intersection; the third member comprises a bore defining a third axis and a second angle and having an upper surface;
- wherein the bore is configured to be accessible to the static pin of the inserter tip for facilitating insertion of the implant and extends from the upper surface into the third member; and further wherein the first angle is defined by the first axis with respect to the second axis and the second angle is defined by the first axis with respect to the third axis;
- wherein the first angle is from 30 degrees to 150 degrees;
- wherein the second angle is from 15 degrees to 90 degrees.

36. The system of claim 23, wherein the lacrimal implant comprises:
- a first member defining a first axis and having a first end along the first axis, wherein the first member is configured to extend into the canaliculus;
- a second member defining a second axis and having a second end along the second axis, wherein the second member is configured to reside in a vertical portion of the canaliculus and to extend to an opening of, or out of the opening of, an associate lacrimal punctum;
- a cavity that is configured to house a therapeutic agent core, wherein the cavity extends into the second member along the second axis;
- a third member connecting the first end of the first member and the second end of the second member at a first angle to form an angled intersection; the third member comprises a bore defining a third axis and a second angle and having an upper surface;
- wherein the bore is configured to be accessible to the static pin of the inserter tip for facilitating insertion of the implant and extends from the upper surface into the third member; and further wherein the first angle is defined by the first axis with respect to the second axis and the second angle is defined by the first axis with respect to the third axis;
- wherein the first angle is from 30 degrees to 150 degrees;
- wherein the second angle is from 15 degrees to 90 degrees.

* * * * *